United States Patent
Langmaid et al.

(10) Patent No.: US 8,382,757 B1
(45) Date of Patent: Feb. 26, 2013

(54) ADJUSTABLE FIXATOR

(75) Inventors: Michael N. Langmaid, West Chester, PA (US); Thomas Joseph Maughan, Hatfield, PA (US); Christoph Andreas Roth, West Chester, PA (US); Michael C. Mazzio, Schwenksville, PA (US)

(73) Assignee: Synthes USA, LLC, West Chester, PA (US)

( * ) Notice: Subject to any disclaimer, the term of this patent is extended or adjusted under 35 U.S.C. 154(b) by 328 days.

(21) Appl. No.: 11/781,590

(22) Filed: Jul. 23, 2007

Related U.S. Application Data

(62) Division of application No. 10/265,258, filed on Oct. 7, 2002, now Pat. No. 7,261,713.

(60) Provisional application No. 60/327,294, filed on Oct. 9, 2001.

(51) Int. Cl.
*A61B 17/64* (2006.01)

(52) U.S. Cl. .......................................... 606/59

(58) Field of Classification Search .............. 606/53–59, 606/60, 246–279, 282, 90, 105; 403/97
See application file for complete search history.

(56) References Cited

U.S. PATENT DOCUMENTS

| | | | |
|---|---|---|---|
| 1,789,060 A | 1/1931 | Weisenbach | |
| 2,238,870 A | 4/1941 | Haynes | |
| 2,391,537 A | 12/1945 | Anderson | |
| 2,393,694 A | 1/1946 | Kirschner | |
| 3,242,922 A | 3/1966 | Thomas | |
| 3,858,578 A | 1/1975 | Milo | |
| 4,019,708 A * | 4/1977 | Croup ........................... 248/137 |
| 4,135,505 A | 1/1979 | Day | |
| 4,208,162 A | 6/1980 | Neitzel | |
| 4,258,708 A | 3/1981 | Gentile | |
| 4,273,116 A | 6/1981 | Chiquet | |
| 4,308,863 A | 1/1982 | Fischer | |
| 4,312,336 A | 1/1982 | Danieletto et al. | |
| 4,365,624 A | 12/1982 | Jaquet | |
| 4,450,834 A | 5/1984 | Fischer | |
| 4,457,300 A | 7/1984 | Budde | |
| 4,475,546 A * | 10/1984 | Patton ............................ 606/57 |
| 4,483,334 A | 11/1984 | Murray | |
| 4,488,542 A | 12/1984 | Helland | |
| RE31,809 E | 1/1985 | Danieletto et al. | |
| 4,573,452 A | 3/1986 | Greenberg | |
| 4,604,997 A | 8/1986 | De Bastiani et al. | |
| 4,611,586 A | 9/1986 | Agee et al. | |

(Continued)

FOREIGN PATENT DOCUMENTS

| | | |
|---|---|---|
| DE | 26 57 303 A1 | 6/1977 |
| DE | 27 05 885 A1 | 8/1978 |

(Continued)

OTHER PUBLICATIONS www.ok-vise.com web pages (15 pages total).

(Continued)

*Primary Examiner* — Eduardo C Robert
*Assistant Examiner* — Jerry Cumberledge
(74) *Attorney, Agent, or Firm* — Fay Kaplun & Marcin, LLP

(57) ABSTRACT

A bone fixator for securing a first bone portion in a position relative to second bone portion is disclosed, including at least two clamping assemblies each for receiving at least one bone pin and a main body disposed between the clamping assemblies. The main body includes at least one joint for orienting the clamping assemblies with respect to each other. The at least one joint may permit pivoting or rotation. Some joints permit the articulation of several components to be simultaneously and releasably lockable.

20 Claims, 20 Drawing Sheets

U.S. PATENT DOCUMENTS

| | | | |
|---|---|---|---|
| 4,620,533 A | 11/1986 | Mears | |
| 4,621,627 A | 11/1986 | DeBastiani et al. | |
| 4,628,919 A | 12/1986 | Clyburn | |
| 4,628,922 A | 12/1986 | Dewar | |
| 4,657,284 A | 4/1987 | Fiori | |
| 4,662,365 A | 5/1987 | Gotzen et al. | |
| 4,714,076 A | 12/1987 | Comte et al. | |
| 4,730,608 A | 3/1988 | Schlein | |
| 4,745,943 A | 5/1988 | Mortensen | |
| 4,848,368 A | 7/1989 | Kronner | |
| 4,895,141 A | 1/1990 | Koeneman et al. | |
| 4,922,896 A | 5/1990 | Agee et al. | |
| 4,944,743 A | 7/1990 | Gotzen et al. | |
| 4,957,495 A | 9/1990 | Kluger | |
| 4,988,349 A | 1/1991 | Pennig | |
| 5,019,077 A | 5/1991 | De Bastiani et al. | |
| 5,026,372 A * | 6/1991 | Sturtzkopf et al. | 606/54 |
| 5,053,034 A | 10/1991 | Olerud | |
| 5,087,258 A | 2/1992 | Schewior | |
| 5,098,432 A | 3/1992 | Wagenknecht | |
| 5,108,393 A | 4/1992 | Ruffa | |
| 5,108,394 A | 4/1992 | Kurokawa et al. | |
| 5,122,140 A | 6/1992 | Asche et al. | |
| 5,152,280 A | 10/1992 | Danieli | |
| 5,160,335 A | 11/1992 | Wagenknecht | |
| 5,167,661 A | 12/1992 | Wagenknecht | |
| 5,207,676 A | 5/1993 | Canadell et al. | |
| 5,209,750 A | 5/1993 | Stef | |
| 5,304,177 A | 4/1994 | Pennig | |
| 5,320,622 A | 6/1994 | Faccioli et al. | |
| 5,376,091 A | 12/1994 | Hotchkiss et al. | |
| 5,405,113 A | 4/1995 | Jaw | |
| 5,405,347 A * | 4/1995 | Lee et al. | 606/54 |
| RE34,985 E | 6/1995 | Pennig | |
| 5,429,637 A | 7/1995 | Hardy | |
| 5,437,667 A | 8/1995 | Papierski et al. | |
| 5,443,465 A | 8/1995 | Pennig | |
| 5,451,226 A | 9/1995 | Pfeil et al. | |
| 5,549,634 A * | 8/1996 | Scott et al. | 606/170 |
| 5,597,566 A * | 1/1997 | Huls | 464/119 |
| 5,620,442 A | 4/1997 | Bailey et al. | |
| 5,649,925 A | 7/1997 | Barbera Alacreu | |
| 5,658,283 A | 8/1997 | Huebner | |
| 5,661,942 A * | 9/1997 | Palmer | 52/653.2 |
| 5,662,648 A | 9/1997 | Faccioli et al. | |
| 5,662,649 A | 9/1997 | Huebner | |
| 5,662,650 A | 9/1997 | Bailey et al. | |
| 5,683,389 A | 11/1997 | Orsak | |
| 5,688,271 A | 11/1997 | Faccioli et al. | |
| 5,702,388 A | 12/1997 | Jackson et al. | |
| 5,707,370 A | 1/1998 | Berki et al. | |
| 5,709,681 A | 1/1998 | Pennig | |
| 5,728,096 A | 3/1998 | Faccioli et al. | |
| 5,738,684 A | 4/1998 | Thomas et al. | |
| 5,741,252 A | 4/1998 | Mazzio et al. | |
| 5,743,898 A | 4/1998 | Bailey et al. | |
| 5,752,954 A | 5/1998 | Mata et al. | |
| 5,768,960 A * | 6/1998 | Archuleta | 81/177.8 |
| 5,769,851 A * | 6/1998 | Veith | 606/57 |
| 5,788,695 A | 8/1998 | Richardson | |
| 5,797,910 A | 8/1998 | Martin | |
| 5,803,924 A | 9/1998 | Oni et al. | |
| 5,810,814 A | 9/1998 | Newson | |
| 5,827,282 A | 10/1998 | Pennig | |
| 5,843,081 A | 12/1998 | Richardson | |
| 5,846,245 A | 12/1998 | McCarthy et al. | |
| 5,891,144 A | 4/1999 | Mata et al. | |
| 5,897,555 A | 4/1999 | Clyburn et al. | |
| 5,899,425 A | 5/1999 | Corey Jr. et al. | |
| 5,902,302 A | 5/1999 | Berki et al. | |
| 5,902,304 A * | 5/1999 | Walker et al. | 606/71 |
| 5,931,837 A | 8/1999 | Marsh et al. | |
| 5,941,877 A | 8/1999 | Viegas et al. | |
| 5,941,879 A | 8/1999 | Walulik et al. | |
| 5,944,719 A | 8/1999 | Leban | |
| 5,951,556 A | 9/1999 | Faccioli et al. | |
| 5,976,136 A | 11/1999 | Bailey et al. | |
| 5,993,448 A | 11/1999 | Remmler | |
| 5,997,537 A * | 12/1999 | Walulik | 606/56 |
| 6,010,501 A | 1/2000 | Raskin et al. | |
| 6,024,745 A | 2/2000 | Faccioli et al. | |
| 6,036,691 A * | 3/2000 | Richardson | 606/57 |
| 6,071,052 A * | 6/2000 | Kerr | 411/302 |
| 6,102,911 A | 8/2000 | Faccioli et al. | |
| 6,152,925 A | 11/2000 | Marsh et al. | |
| 6,171,308 B1 | 1/2001 | Bailey et al. | |
| 6,176,860 B1 | 1/2001 | Howard | |
| 6,176,882 B1 | 1/2001 | Biedermann et al. | |
| 6,214,004 B1 | 4/2001 | Coker | |
| 6,217,577 B1 | 4/2001 | Hofmann | |
| 6,224,597 B1 | 5/2001 | Coker | |
| 6,235,029 B1 * | 5/2001 | Faccioli et al. | 606/54 |
| 6,241,730 B1 | 6/2001 | Alby | |
| 6,244,780 B1 * | 6/2001 | Hansson | 403/374.3 |
| 6,245,071 B1 | 6/2001 | Pierson | |
| 6,245,075 B1 | 6/2001 | Betz et al. | |
| 6,261,287 B1 | 7/2001 | Metz-Stavenhagen | |
| 6,264,658 B1 | 7/2001 | Lee et al. | |
| 6,267,764 B1 | 7/2001 | Elberg | |
| 6,267,765 B1 | 7/2001 | Taylor et al. | |
| 6,273,914 B1 | 8/2001 | Papas | |
| 6,277,118 B1 | 8/2001 | Grant et al. | |
| 6,277,119 B1 | 8/2001 | Walulik et al. | |
| 6,283,964 B1 | 9/2001 | Weiner | |
| 6,283,967 B1 | 9/2001 | Troxell et al. | |
| 6,296,644 B1 | 10/2001 | Saurat et al. | |
| 6,299,614 B1 | 10/2001 | Kretschmer et al. | |
| 6,302,882 B1 | 10/2001 | Lin et al. | |
| 6,302,888 B1 | 10/2001 | Mellinger et al. | |
| 6,306,137 B2 | 10/2001 | Troxell | |
| 6,309,389 B1 | 10/2001 | Baccelli | |
| 6,309,390 B1 | 10/2001 | Le Couedic et al. | |
| 6,309,391 B1 | 10/2001 | Crandall et al. | |
| 6,322,566 B1 | 11/2001 | Minoretti et al. | |
| 6,328,737 B1 | 12/2001 | Moorcroft et al. | |
| 6,328,741 B1 * | 12/2001 | Richelsoph | 606/252 |
| 6,332,780 B1 | 12/2001 | Traxel et al. | |
| 6,340,361 B1 | 1/2002 | Kraus et al. | |
| 6,342,054 B1 | 1/2002 | Mata | |
| 6,386,786 B1 | 5/2002 | Perlman et al. | |
| 6,409,729 B1 | 6/2002 | Martinelli et al. | |
| 6,428,540 B1 | 8/2002 | Claes et al. | |
| 2001/0034520 A1 | 10/2001 | Enayati | |
| 2001/0049525 A1 | 12/2001 | Slocum | |
| 2001/0049526 A1 | 12/2001 | Venturini et al. | |
| 2001/0051806 A1 | 12/2001 | Ballier | |
| 2001/0053911 A1 | 12/2001 | Hehli et al. | |
| 2002/0004659 A1 | 1/2002 | Boudard et al. | |
| 2002/0007183 A1 | 1/2002 | Lee et al. | |
| 2002/0010465 A1 | 1/2002 | Koo et al. | |
| 2002/0013584 A1 | 1/2002 | Termaten | |

FOREIGN PATENT DOCUMENTS

| | | |
|---|---|---|
| DE | 31 41 909 A1 | 6/1982 |
| DE | 38 07 335 A1 | 9/1989 |
| DE | 43 13 767 A1 | 11/1993 |
| DE | 197 46 687 A1 | 5/1999 |
| DE | 198 07 236 A1 | 9/1999 |
| EP | 0 153 546 AI | 9/1985 |
| EP | 0 807 419 A2 | 11/1997 |
| EP | 0 858 781 A2 | 8/1998 |
| FR | 2 705 881 | 12/1994 |
| JP | 10-225466 | 8/1998 |
| SU | 1333327 A1 | 8/1987 |
| WO | WO 88/03395 | 5/1988 |
| WO | WO 90/07305 | 7/1990 |
| WO | WO 90/11727 | 10/1990 |
| WO | WO 91/11150 | 8/1991 |
| WO | WO 93/08758 | 5/1993 |
| WO | WO 94/23662 | 10/1994 |
| WO | WO 96/19943 | 7/1996 |
| WO | WO 98/20802 | 5/1998 |
| WO | WO 99/20194 | 4/1999 |
| WO | WO 99/59489 | 11/1999 |

OTHER PUBLICATIONS www.miteebite.com web pages (4 pages total).

Mitee-Bite Products Inc. brochure (1 page).
The Titanium Multi-Vector Distractor Technique Guide, Synthes® Maxillofacial, Jun. 1999 (16 pages).
Instruments + Implants brochure, Synthes® (10 pages).
Synthes® fixation brochure, including "Applications," "Operative Technique," "Repositioning in all planes" (6 pages).
ACE Align™ brochure, ACE Medical Company, 1995 (2 pages).
ACE Align™ Surgical Technique, ACE Medical Company, 1995 (12 pages).
The Ace-Fischer® Fixator, ACE Medical, Jan. 1985 (4 pages).

R. Aldegheri et al., Orthofix® Modulsystem Operative Technique, Limb Lengthening and Correction of Deformities by Callus Distraction (38 pages).
Torus™ External Fixation System Surgical Techniques, External Fixation of the Long Bones and Pelvis, brochure (5 pages).
www.smithnephew.com web page, "Heidelberg Fixator" (1 page).
Heidelberg Quick Reference Guide, Smith & Nephew, Inc., Dec. 1998 (2 pages).

* cited by examiner

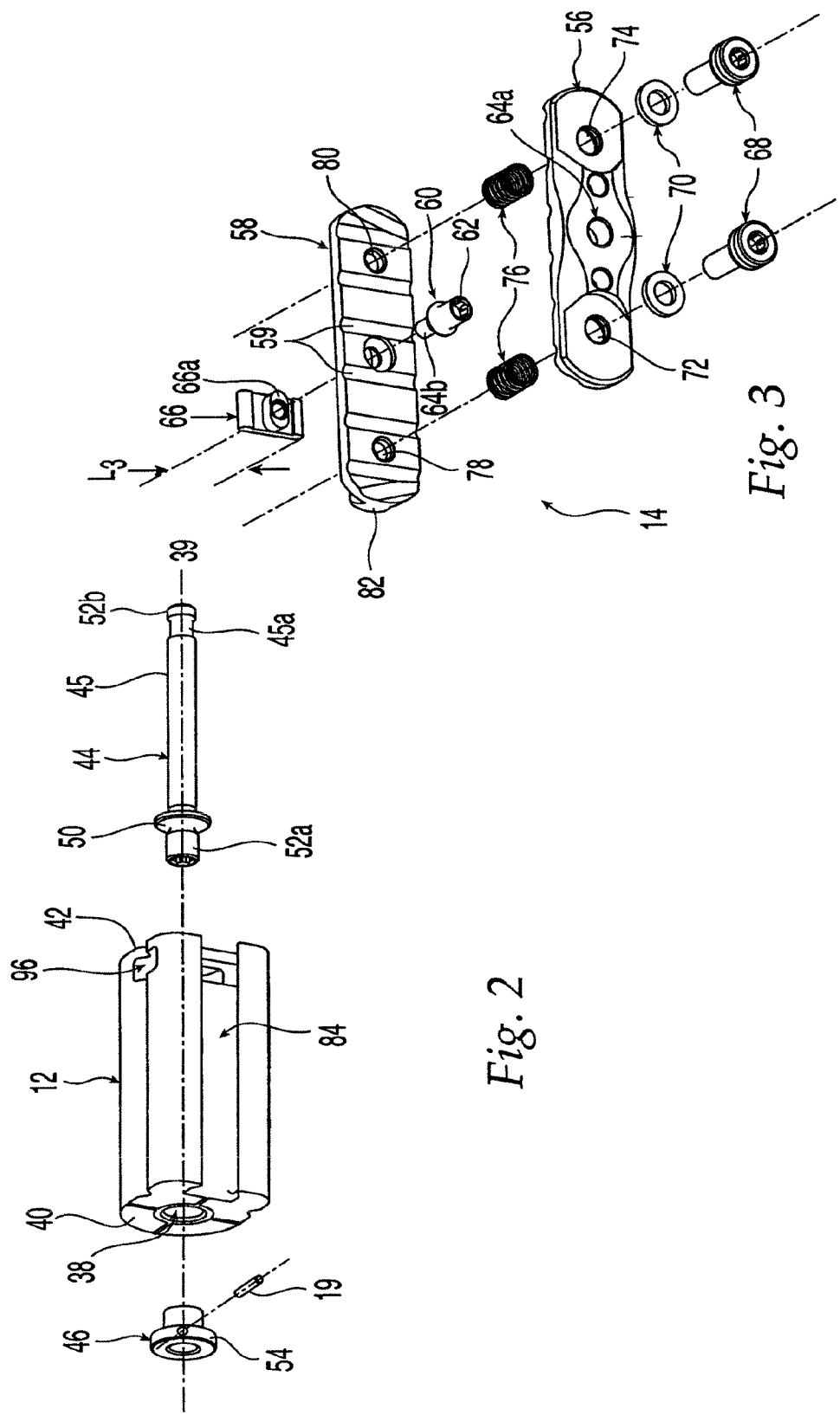

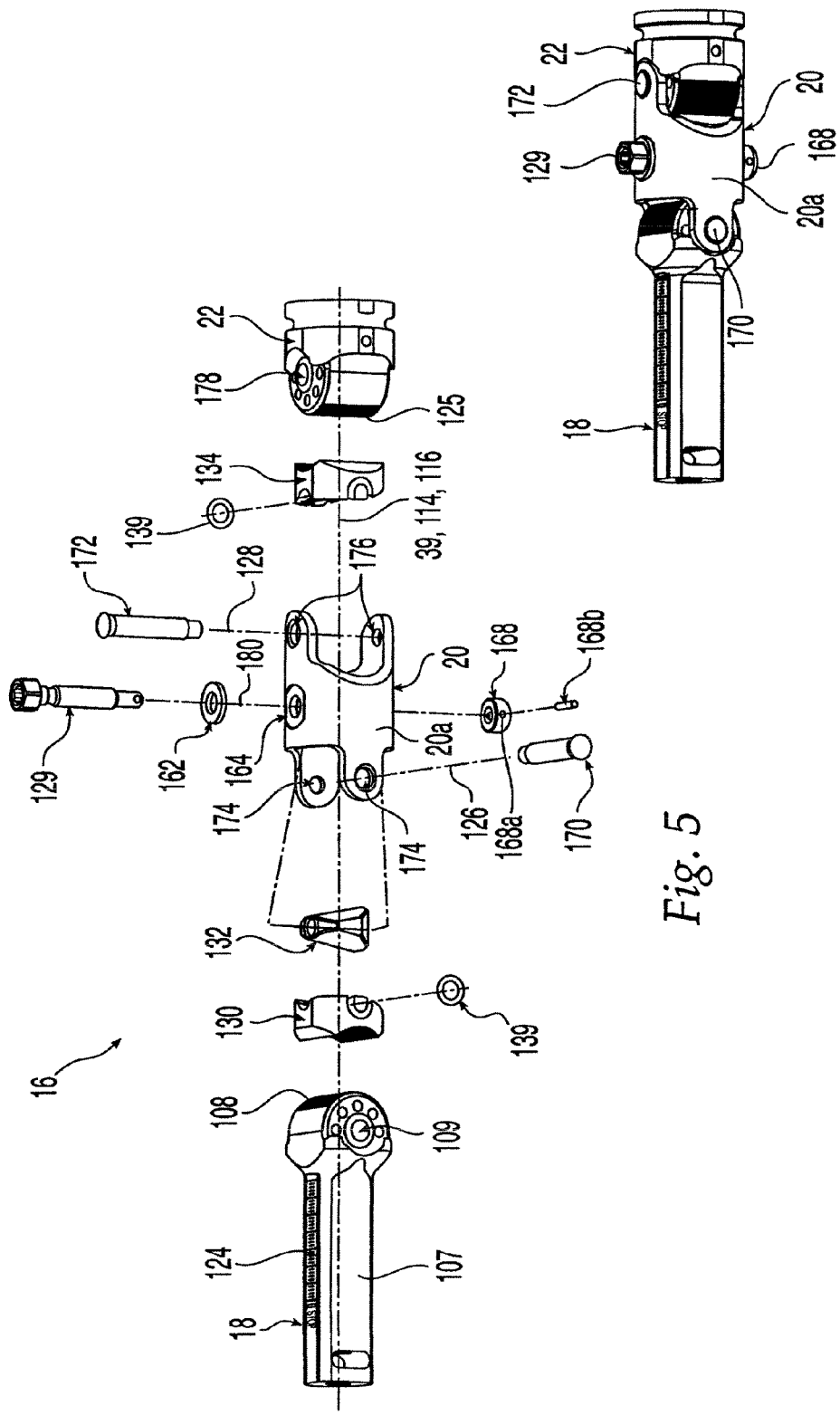

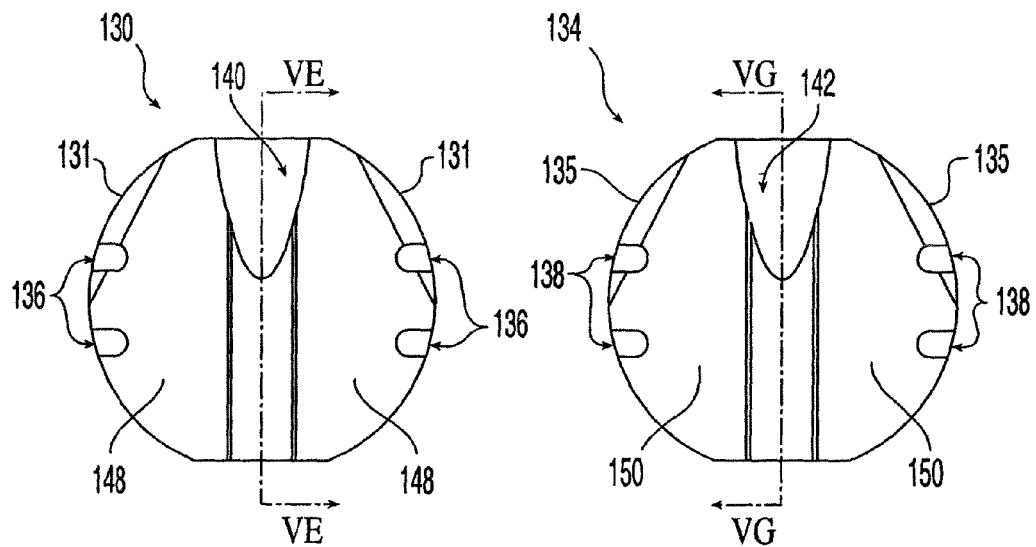
*Fig. 5D*  *Fig. 5F*
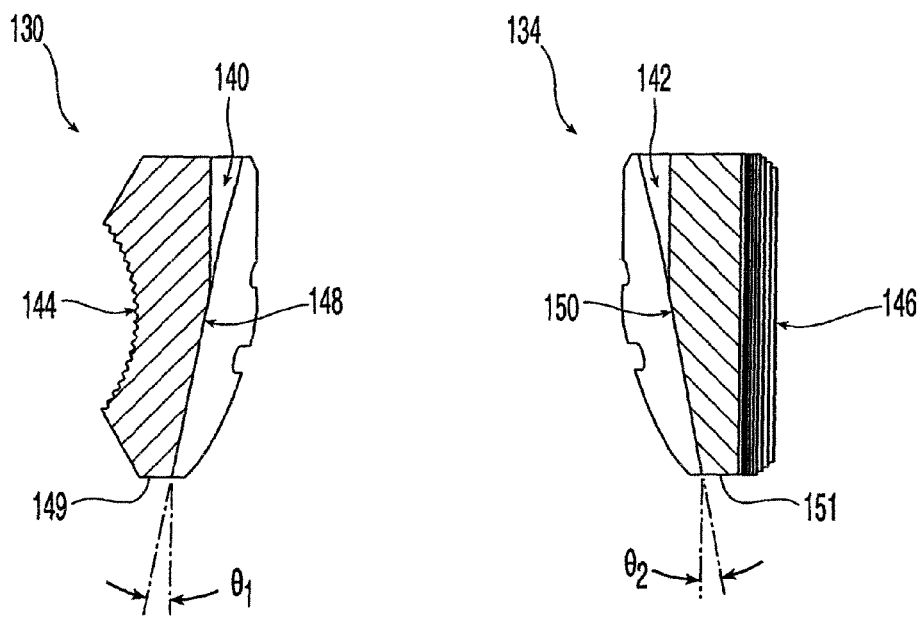
*Fig. 5E*  *Fig. 5G*

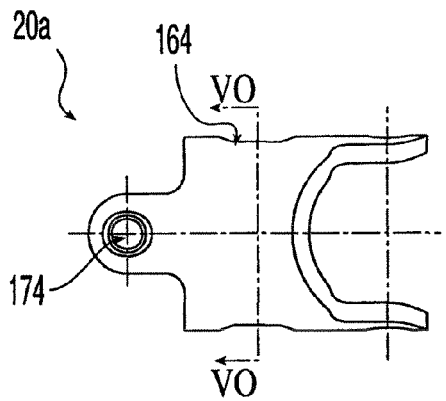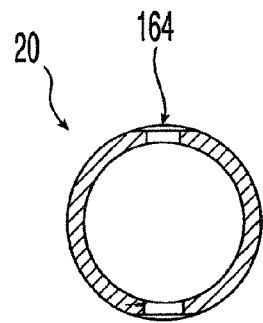
Fig. 5N  Fig. 5O
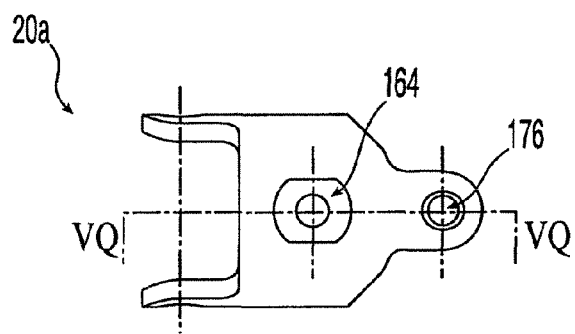
Fig. 5P
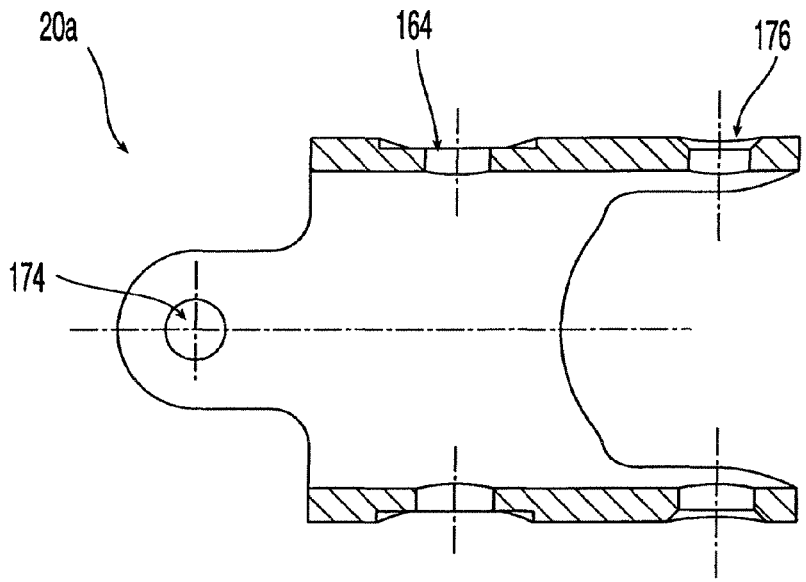
Fig. 5Q

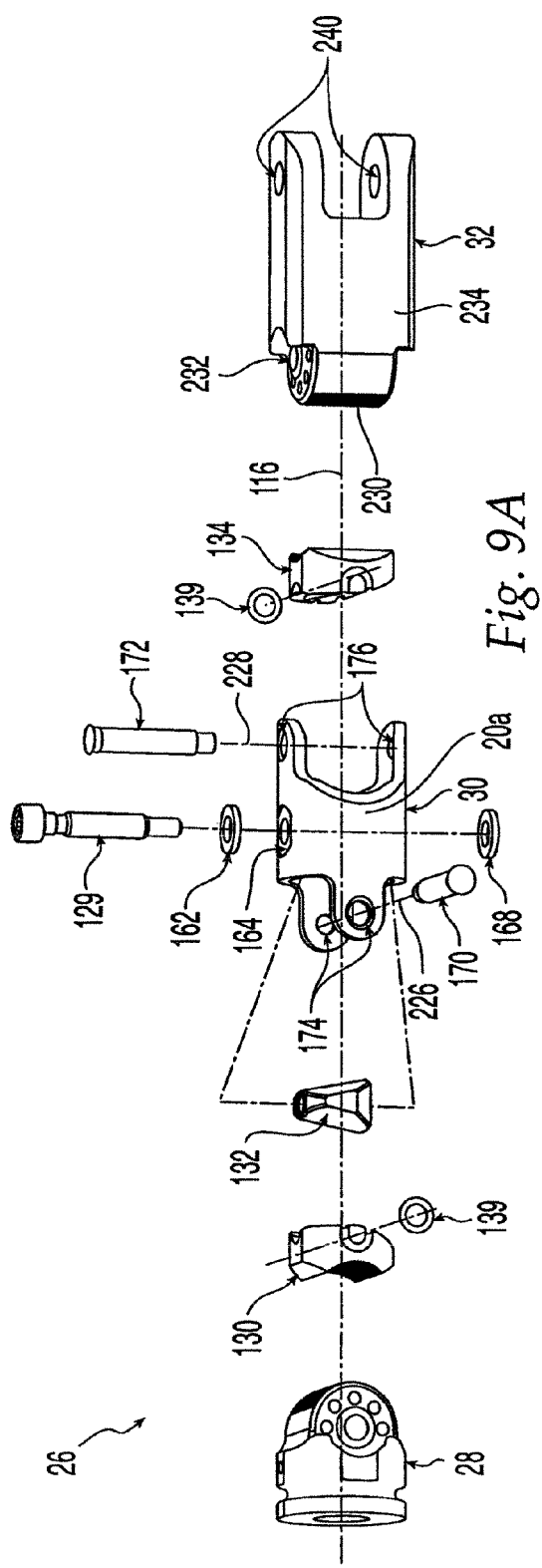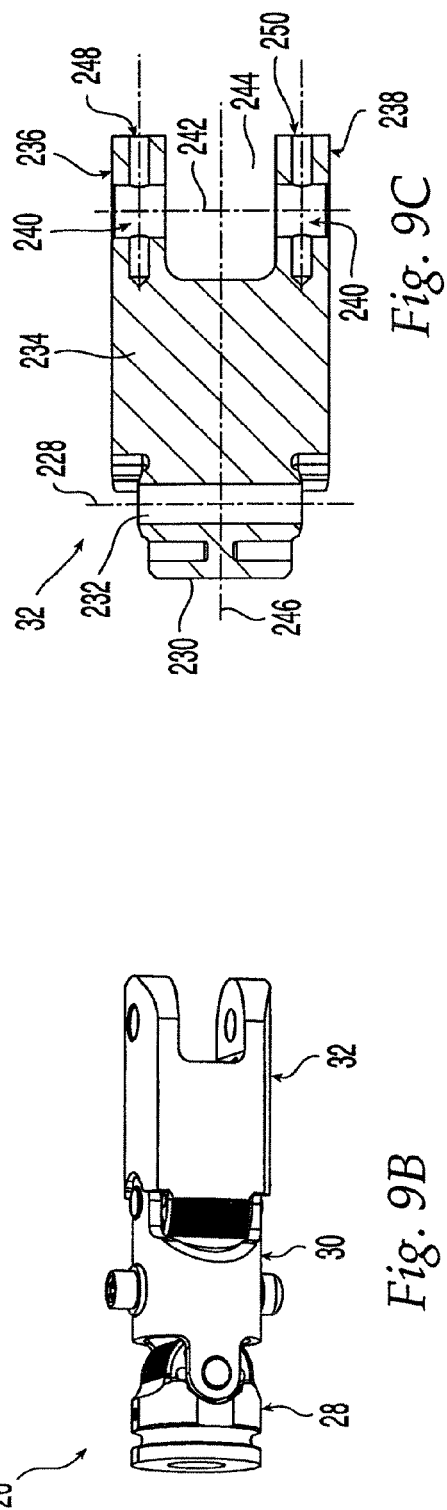

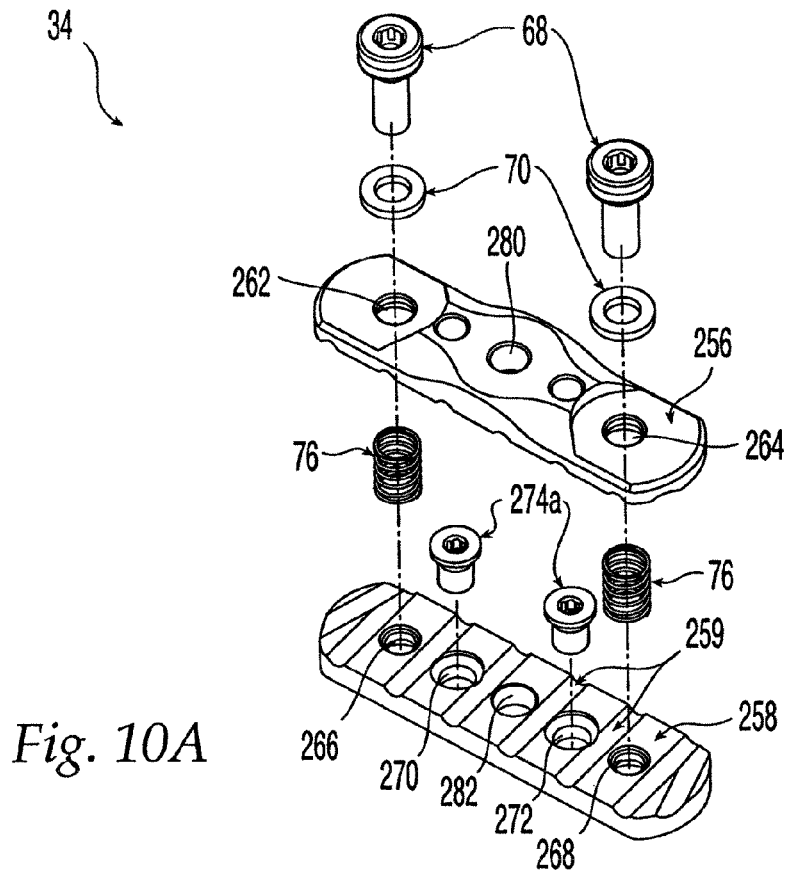
*Fig. 10A*
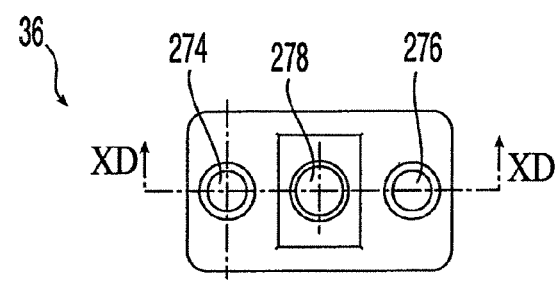
*Fig. 10B*
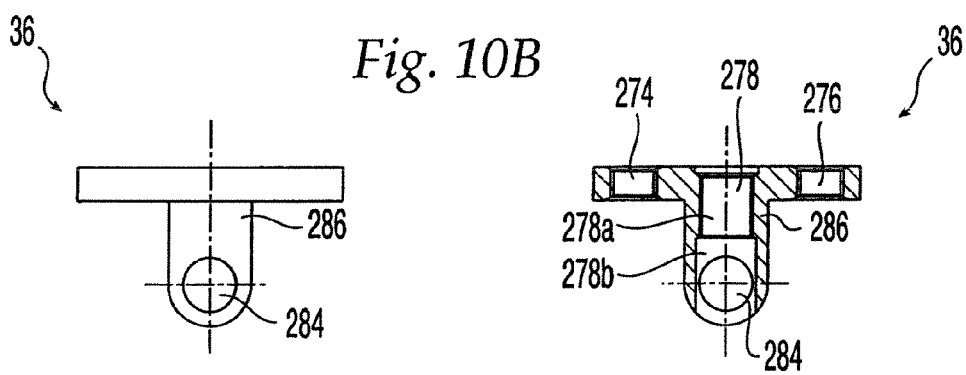
*Fig. 10C*          *Fig. 10D*

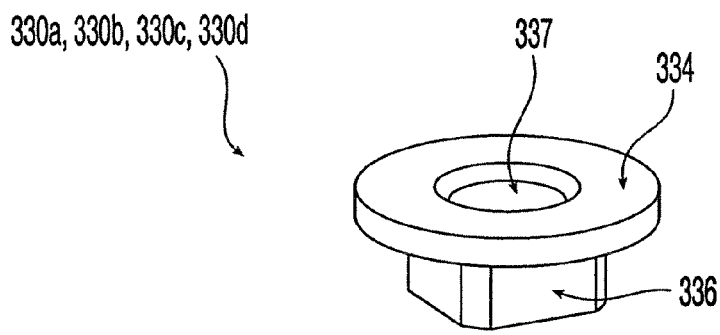
Fig. 12G
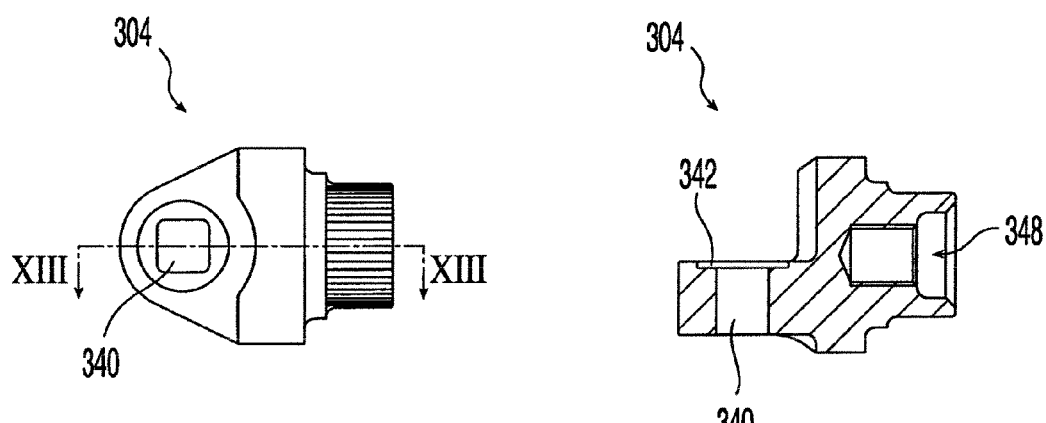
Fig. 12H
Fig. 12I
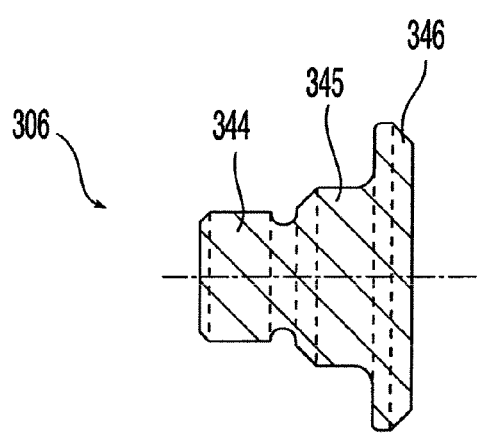
Fig. 12J

ADJUSTABLE FIXATOR

CROSS-REFERENCE TO RELATED APPLICATIONS

The present application is a divisional of U.S. patent application Ser. No. 10/265,258, filed Oct. 7, 2002, which claims the benefit of U.S. Provisional Application No. 60/327,294, filed Oct. 9, 2001, the entire contents of both of which are expressly incorporated herein by reference.

FIELD OF THE INVENTION

The present invention relates generally to orthopaedic surgical devices, and more particularly to an adjustable fixator for securing bone segments.

BACKGROUND OF THE INVENTION

Various types of orthopaedic devices are known for the fixation of bone fragments. Such devices typically are used to stabilize bones by maintaining fractured bone portions in relatively fixed positions with respect to each other. The alignment and stability provided by the devices promotes the healing of fractures, allowing proper fusion to occur.

Internal fixation devices include bone screws, which are used in a variety of orthopaedic applications for fixation of bone fragments. Bone fragments may be positioned in a desired configuration, and one or more holes may be drilled and tapped across the fracture. Compression and stabilization of the bone fragments may then be effected by screwing bone screws into the holes. One limitation associated with bone screws, however, is that repositioning or adjusting the bone screws following implantation is difficult. In order to accommodate a different alignment, it is often necessary to remove the original bone screws and drill new holes for subsequent bone screw implantation.

Metal pins also are often used to stabilize bones. Similar to bone screws, metal pins may be inserted in holes drilled across bone fragments to confer stability to the bone. However, as with bone screws, removal of the pins may be required if subsequent realignment of bone portions is necessary.

Intramedullary implants are another device used for fixation of bone fragments. Such a device may be placed in the central canal of a fractured bone and locked thereto at the longitudinal ends of the device using screws. The use of intramedullary implants is very invasive, though, and the implants are difficult to manipulate once installed within the canals of bone fragments.

External fixation devices also are commonly used to stabilize bone segments. These devices employ a plurality of pins which extend through a patient's skin into holes drilled in fractured bone. Clamps are used to secure the pins to a common apparatus, which may for example take the form of a rod that is disposed generally parallel to the anatomically correct longitudinal axis of the fractured bone. The clamps in combination with the common apparatus create a rigid frame for immobilizing the fracture to promote healing.

External skeletal fixation is a preferred method of treatment for various limb deformities, injuries, and other conditions including: severe open fractures, fractures associated with severe burns, fractures requiring distraction, fractures requiring limb lengthening, arthrodesis, infected fractures, and nonunions. External fixation offers several advantages over the above-mentioned internal fixation approaches. For example, external fixation enables skeletal stabilization to be managed from a location that is generally remote from the proximity of deformity, injury, or disease, thereby permitting direct surveillance of the limb and wound during related or subsequent procedures. In addition, external fixation facilitates adjustment of fracture alignment, bone lengthening, bone compression, and fixed distraction following initial surgery. Furthermore, minimal interference with proximal and distal joints allows immediate mobilization of a wounded limb, and insertion of the fixator pins can be performed under local anesthesia.

Despite these developments, there remains a need for fixation devices with improved adjustability. In particular, there remains a need for fixation devices with improved joints and overall constructions.

SUMMARY OF THE INVENTION

The invention relates to a bone fixator including at least two clamping assemblies each for receiving at least one bone fastener. The bone fixator includes a main body having first and second ends, a first coupling member, and a second coupling member. The first coupling member may be pivotably coupled to the first end of the main body about a first axis, and the second coupling member may be pivotably coupled to the second end of the main body about a second axis. A wedge may be disposed within the main body, and may have a borehole disposed along a translation axis. A locking member may be disposed along the translation axis and may be operatively associated with the wedge. A first moveable element may be disposed between the first coupling member and the wedge, and a second moveable element may be disposed between the second coupling member and the wedge. The wedge may be engageable with the moveable elements to arrest pivoting of the coupling members and disengageable from the moveable elements to permit pivoting thereof with respect to the main body. In some embodiments, the first and second axes may be disposed transverse to each other, and in one embodiment, the first and second axes are disposed substantially perpendicular to each other.

The borehole and locking member may be threadably associated with each other. Further, the locking member may be fixed in position along the translation axis and rotatable thereabout. The moveable elements may be slidably associated with the wedge.

At least one of the coupling members and at least one of the locking members may each have textured portions, with the textured portion of the at least one coupling member being positively lockable with the textured portion of the at least one locking member. The textured portions may include textures selected from serrations and facets. At least a portion of the main body may have an inner cylindrical surface and the moveable elements may be configured and dimensioned to be slidably associated with the cylindrical surface. The moveable elements may be resiliently biased toward each other.

The wedge may have first and second outer engagement surfaces disposed transverse to each other. In some embodiments, the first and second outer engagement surfaces are disposed at an angle of between about 10° and about 70°. In one embodiment, the first and second outer engagement surfaces may be disposed at an angle of about 22°.

The moveable elements each may have an inner engagement surface, and the engagement surfaces of the moveable elements may be disposed at about the same angle as the first and second outer engagement surfaces of the wedge.

At least one of the clamping assemblies may be operatively associated with the first coupling member. The at least one clamping assembly may be translatable with respect to the first coupling member.

A distractor body may be operatively associated with the first coupling member of the bone fixator, with at least one of the clamping assemblies being operatively associated with the distractor body. At least one clamping assembly may be translatable with respect to the distractor body and releasably lockable thereto. At least one of the clamping assemblies may include at least one of the first or second coupling members.

The bone fixator may further include a joint assembly having a joint assembly body with a borehole extending therethrough along a borehole axis and a fastener hole extending along a fastener axis transverse to the borehole axis. The body may have an outer surface and an inner borehole surface. A slit may extend along the borehole axis and across the fastener hole from the outer surface to the inner borehole surface, with the slit defining opposed slit surfaces having a separation width. The joint assembly also may include a fastener configured and dimensioned to be received in the fastener hole. The size of the borehole may be adjustable by changing the separation width of the opposed slit surfaces. The joint assembly body may further include at least one rib disposed radially on the inner borehole surface, and the second coupling member may be retained in the joint assembly by the rib. In addition, a second rib may be provided on the joint assembly body, and a third coupling member may be retained in the joint assembly by the second rib.

The second and third coupling members may have opposed surfaces disposed in the borehole that are coupled together by an insert member. The insert member may extend within recessed portions of the second and third coupling members. A link member may be disposed between the third coupling member and a second of the clamping assemblies. The link member may be pivotably associated with the second clamping assembly.

The slit of the joint assembly body may include first and second sections, with the sections being oriented at an angle of between about 20° and 50° with respect to each other. The joint assembly may be formed of a fiber-reinforced polymer.

The bone fixator may further include a second main body having a second wedge, a second locking member, a third moveable element, and a fourth moveable element.

The invention also relates to a bone fixator including at least two clamping assemblies each for receiving at least one bone fastener. The bone fixator may further include a main body disposed between the clamping assemblies, with the main body having a joint assembly. The joint assembly may include (1) a male segment having first and second ends and a projection extending from the second end, (2) a female segment having first and second ends, a cavity disposed proximate the first end and configured and dimensioned to receive at least a portion of the projection, and an opening connected to the cavity, and (3) a cover piece configured and dimensioned to be received in the opening. When the male segment is inserted in the female segment and the cover piece is disposed in the opening, the cover piece resists removal of the projection and the male segment is releasably rotatable with respect to the female segment.

The projection may include a serrated cylindrical portion and the cover piece may include a serrated arcuate inner surface, with the serrated cylindrical portion and the serrated arcuate inner surface are mutually positively lockable. The female segment may further include a fastener hole and the cover piece may further include a cover piece hole, with the holes being coaxial when the cover piece is disposed in the opening.

The bone fixator also may include a fastener, so that when the fastener is disposed in the coaxial fastener hole and cover piece hole, the cover piece is securable to the female segment.

In addition, the bone fixator may include at least one tension clamp. The tension clamp may include a body having a borehole extending therethrough along a borehole axis and a fastener hole extending along a fastener axis transverse to the borehole axis, with the body having an outer surface and an inner borehole surface. A slit may extend along the borehole and across the fastener hole from the outer surface to the inner borehole surface, with the slit defining opposed slit surfaces having a separation width. A fastener may be configured and dimensioned to be received in the fastener hole, and the size of the borehole may be adjustable by changing the separation width of the opposed slit surfaces.

The present invention further relates to a bone fixator including at least two clamping assemblies each for receiving at least one bone fastener, and a main body disposed between the clamping assemblies, with the main body having at least one joint selected from the group consisting of: (1) a first joint including a main body having first and second ends, a first coupling member pivotably coupled to the first end and a second coupling member pivotably coupled to the second end, a wedge disposed within the main body having a borehole disposed along a translation axis, a locking member disposed along the translation axis and operatively associated with the wedge, a first moveable element disposed between the first coupling member and the wedge, a second moveable element disposed between the second coupling member and the wedge, with the wedge being engageable with the moveable elements to arrest pivoting of the coupling members and disengageable from the moveable elements to permit pivoting thereof with respect to the main body; (2) a second joint including a joint assembly body having an outer surface and a borehole extending therethrough along a borehole axis forming an inner borehole surface, and a fastener hole extending along a fastener axis transverse to the borehole axis, a slit extending substantially along the direction of the borehole and across the fastener hole from the outer surface to the inner borehole surface and defining opposed slit surfaces having a separation width, with the size of the borehole being adjustable by changing the separation width of the opposed slit surfaces; and (3) a third joint including a male segment having a projection extending from an end thereof, a female segment having a cavity disposed proximate an end thereof and an opening connected to the cavity, the cavity being configured and dimensioned to receive at least a portion of the projection, and a cover piece configured and dimensioned to be received in the opening, wherein when the male segment is inserted in the female segment and the cover piece is disposed in the opening, the cover piece resists removal of the projection and the male segment is releasably rotatable with respect to the female segment. The main body of the bone fixator may include at least two different joints selected from the first joint, the second joint, and the third joint. In one embodiment, the main body comprises at least one first joint and at least one second joint.

BRIEF DESCRIPTION OF THE DRAWINGS

Preferred features of the present invention are disclosed in the accompanying drawings, wherein similar reference characters denote similar elements throughout the several views, and wherein:

FIG. 2 shows an exploded view of the distractor body of FIG. 1;

FIG. 3 shows an exploded view of the distractor clamp assembly of FIG. 1;

FIG. 5 shows an exploded perspective view of the first body portion of FIG. 1;

FIG. 5A shows an assembled perspective view of the first body portion of FIG. 5;

FIG. 5D shows a side view of a first lock piece of FIG. 1;

FIG. 5E shows a cross-sectional view along line VE-VE of a first lock piece of FIG. 1;

FIG. 5F shows a side view of a second lock piece of FIG. 1;

FIG. 5G shows a cross-sectional view along line VG-VG of a second lock piece of FIG. 1;

FIG. 5N shows a side view of the body joint of distractor joint assembly of FIG. 1;

FIG. 5O shows a cross-sectional view of the body joint of distractor joint assembly of FIG. 5N along line VO-VO;

FIG. 5P shows another side view of the body joint of distractor joint assembly of FIG. 5N;

FIG. 5Q shows a cross-sectional view of the body joint of distractor joint assembly of FIG. 5I) along line VQ-VQ;

FIG. 9A shows an exploded perspective view of the second body portion of FIG. 1;

FIG. 9B shows an assembled perspective view of the second body portion of FIG. 9A;

FIG. 9C shows a cross-sectional view of the T-clamp link of FIG. 9A;

FIG. 10A shows an exploded perspective view of the T-clamp assembly of FIG. 1;

FIG. 10B shows a top view of the T-clamp pivot of FIG. 1;

FIG. 10C shows a side view of the T-clamp pivot of FIG. 10B;

FIG. 10D shows a cross-sectional view along line XD-XD of the T-clamp pivot of FIG. 10B;

FIG. 12G shows a perspective view of a insert nut of FIG. 11;

FIG. 12H shows a top view of the first rotatable segment of FIG. 11;

FIG. 12I shows a cross-sectional view of the first rotatable segment of FIG. 12H along line XII I-XII I;

FIG. 12J shows a cross sectional view of the rotatable segment cap of FIG. 11 along a central longitudinal plane;

DETAILED DESCRIPTION OF THE PREFERRED EMBODIMENT

Figure 1:
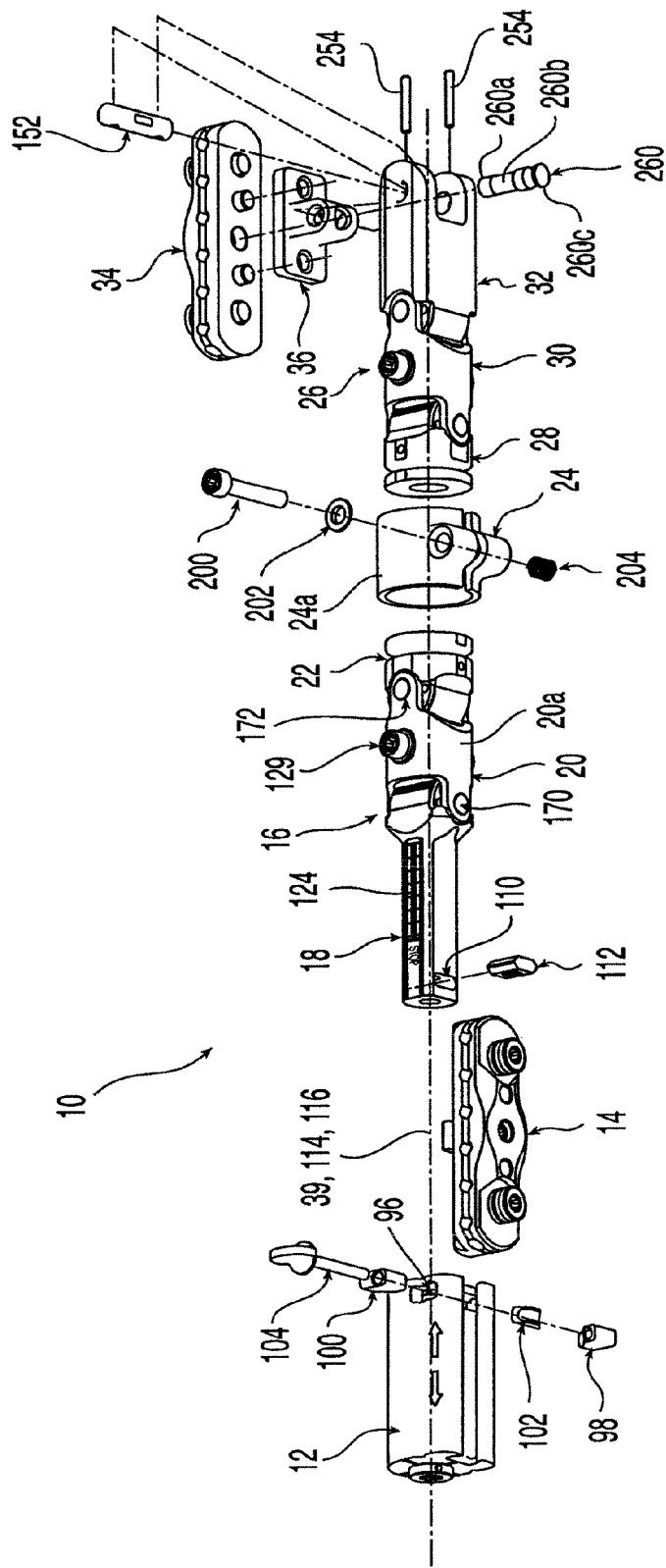
FIG. 1 shows an exploded view of one embodiment of an apparatus for the external fixation of bones.

Referring initially to FIG. 1, an adjustable fixator 10 according to one embodiment of the present invention is shown. Fixator 10 is suitable for stabilizing and rigidly fixing bone fragments or segments with respect to each other, and may be made of any suitable material such as titanium, stainless steel, polymers, alloys, composites, or other materials. Fixator 10 includes a distractor body 12 and associated distractor clamp assembly 14, as well as a first body portion 16 with a distractor bar 18, distractor joint assembly 20, and coupling 22. Distractor body 12 and associated components may be used for distraction and compression. In addition, fixator 10 includes a central joint assembly 24, along with a second body portion 26 having a coupling 28, a T-clamp joint assembly 30, and a T-clamp link 32. A T-clamp assembly 34 is preferably secured to a T-clamp pivot 36 that is pivotably associated with T-clamp link 32.

Turning to FIGS. 2 and 2A-2C, distractor body 12 includes a central through-hole 38 extending along an axis 39 from first end 40 to second end 42. A distractor screw 44 with at least a partially threaded body 45 is disposed about axis 39 and received in through-hole 38. Distractor screw 44 is rotatably associated with first end 40 of distractor body 12 using a distractor screw collar 46 that may be pinned to distractor screw 44 as with a dowel pin 19. Preferably, dowel pin 19 rigidly fixes distractor screw collar 46 to distractor screw 44 such that rotation of screw 44 rotates collar 46. Distractor body 12 includes a stop 48 against which bears shoulder 50 of screw 44. Head 52a of screw 44 extends within first end 40, and is received in collar 46. Preferably, head 52a includes a hexagonal or other shaped recessed region that may be engaged by a suitably shaped tool, such as a hexagonal key. Thus, with head 54 bearing against first end 40, and shoulder 50 bearing against stop 48, screw 44 may be turned about axis 39 while remaining in a longitudinally fixed position with respect to distractor body 12.

As shown in FIG. 3, distractor clamp assembly 14 includes opposing front and rear vise plates 56, 58, respectively each having grooves 59 for receiving bone fasteners. Plates 56, 58 are aligned with distractor lock screw 60, the head 62 of which preferably may be slidably received in central through-hole 64a of front vise plate 56, and the shank 64b of which preferably may be threadably received in distractor nut 66. Vise plates 56, 58 are additionally coupled together with a pair of vise screws 68 each having a vise washer 70. Vise screws 68 extend through holes 72, 74, within respective compression springs 76, and preferably may be threadably received in holes 78, 80 in rear vise plate 58. Thus, it should be noted that until vise plates 56, 58 of distractor clamp assembly 14 are tightened with respect to each other, springs 76 bias vise plates 56, 58 away from each other while permitting vise plates 56, 58 generally to be disposed in either parallel or non-parallel planes as a function of the degree of tightening of each vise screw 68. The upper and lower ends of springs 76 also may abut recessed regions in vise plates 56, 58. Compression springs 76 preferably may be formed of stainless steel and have a spring rate of about 0.16 kg/mm. The distractor clamp assembly 14 receives bone fasteners, for example bone pins or bone screws, which are inserted into bone.

Distractor clamp assembly 14 is demountably coupled to distractor body 12 by inserting rail portion 82 in groove 84 of distractor body 12. As shown particularly in FIGS. 2A and 2B, groove 84 has a maximum width $L_1$ at first end 40, while along the remainder of distractor body 12, groove 84 has a maximum width $L_2$ that is greater than length $L_1$. Preferably, distractor nut 66, which abuts rear vise plate 58, rides in groove 84 on flat face 86 so that the travel of plate 58 is arrested when distractor nut 66 reaches first end 40. Because length $L_3$ of distractor nut 66 is greater than length $L_1$ of groove 84 at first end 40, distractor clamp assembly 14 is prevented from uncoupling by sliding in the direction of first end 40. Moreover, movement of distractor clamp assembly 14 with respect to distractor body 12 is permitted because length $L_3$ of distractor nut 66 is about the same as length $L_2$ of groove 84 in distractor body 12. In addition, rail portion 82 preferably may be sized to be slidably received in groove 84 while abutting upper faces 88, 90 of groove 84. Faces 88, 90 are disposed in transverse planes such that rail portion 82 is retained in groove 84. To fix the position of distractor clamp assembly 14, distractor lock screw 60 is tightened to bring distractor nut 66 firmly against overhangs 92, 94 of groove 84 in distractor body 12. Distractor nut 66 may include an oblong projection 66a proximate the threaded hole therein, with projection 66a being configured and dimensioned to mate within a like-shaped recess in rear vise plate 58 to thereby prevent rotation of distractor nut 66 with respect to rear vise plate 58.

Figure 2A:
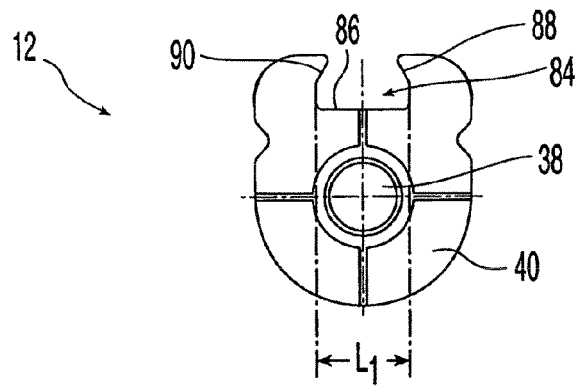
FIG. 2A shows a side view at one end of the distractor body of FIG. 2.
Figure 2B:
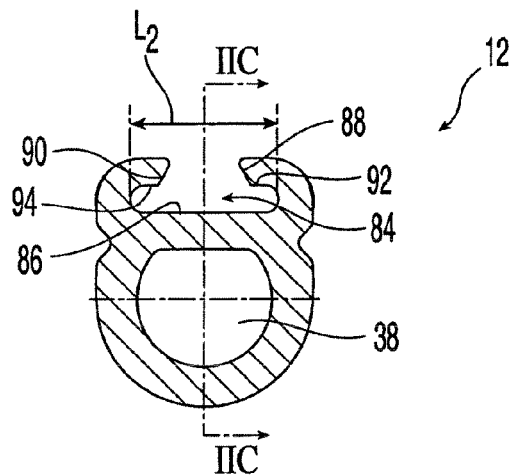
FIG. 2B shows a cross-sectional view of the distractor body of FIG. 2 intermediate to the ends of the body.
Figure 2C:
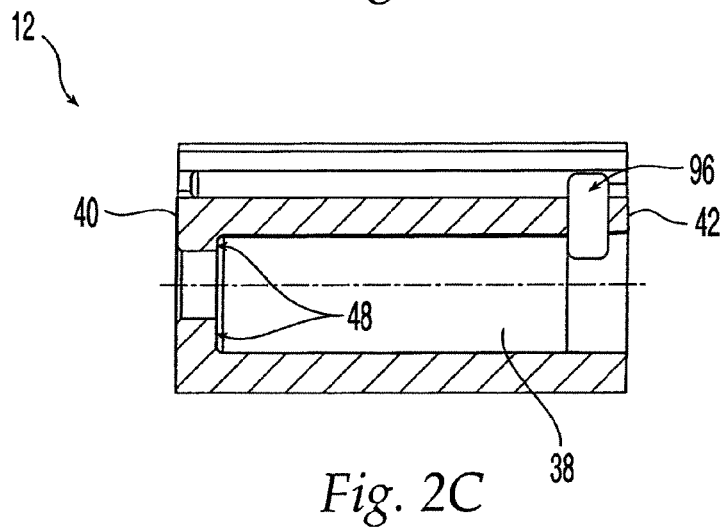
FIG. 2C shows a cross-sectional view of the distractor body of FIG. 2 along line IIC-IIC.
Figure 2D:
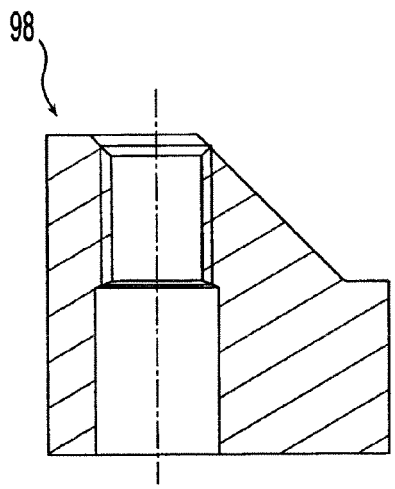
FIG. 2D shows a lock piece of FIG. 1.
Figure 2E:
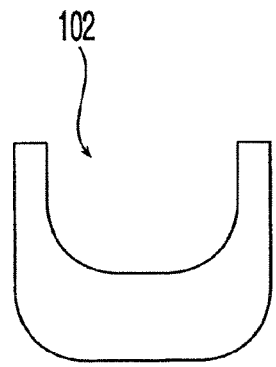
FIG. 2E shows a lock bar of FIG. 1.
Figure 2F:
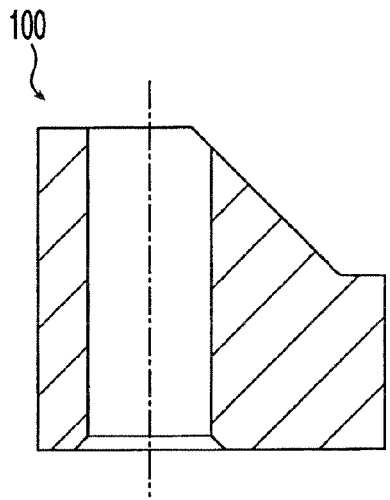
FIG. 2F shows another lock piece of FIG. 1.
Figure 2G:
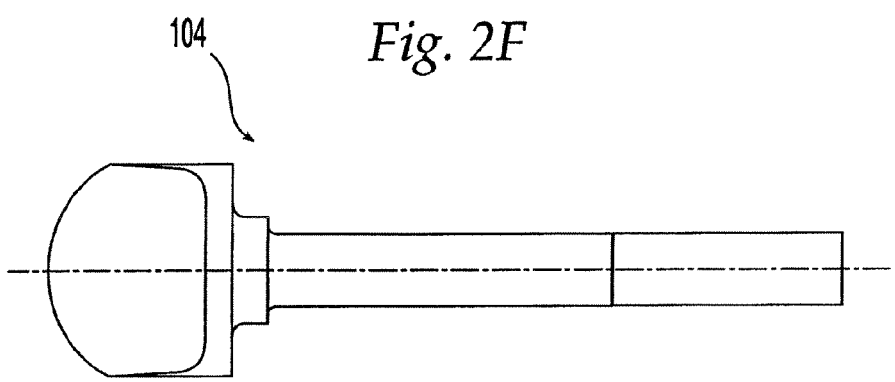
FIG. 2G shows a lock screw of FIG. 1.

As shown in FIGS. 1, 2 and 2C, distractor body 12 is preferably provided with a through-slot 96 in which are disposed opposing lock pieces 98, 100 with a lock bar 102 positioned therebetween. A threaded distractor lock screw 104 is received in lock piece 100 and threadably received in lock piece 98, so that once lock pieces 98, 100 and lock bar 102 are drawn toward and abut each other, the travel of distractor clamp assembly 14 may be arrested when distractor nut 66 comes in contact therewith. These components are shown in detail in FIGS. 2D-2G.

Figure 4A:
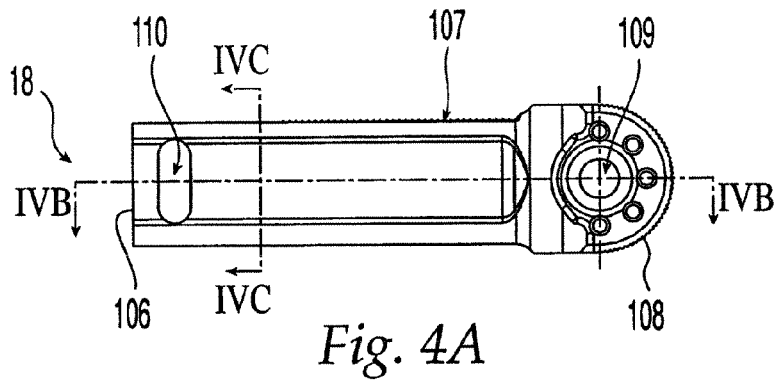
FIG. 4A shows a side view of the distractor bar of FIG. 1.
Figure 4B:
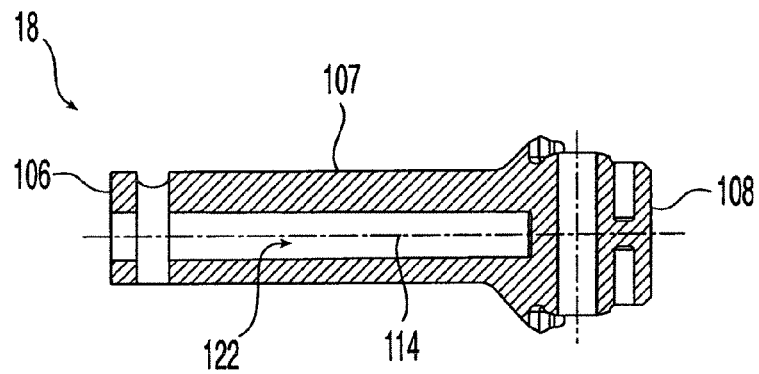
FIGS. 4B and 4C show cross-sectional views of the distractor bar of FIG. 4A along line IVB-IVB and IVC-IVC, respectively.
Figure 4C:
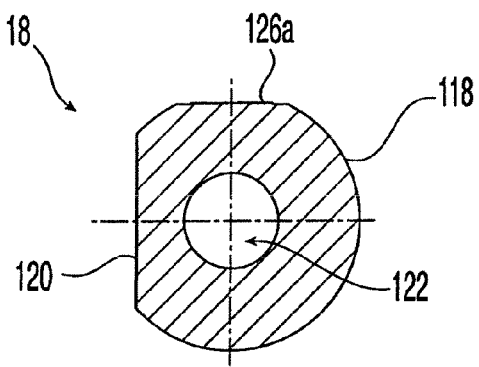

Turning now to FIGS. 4A-4C, distractor bar 18 is shown with a generally flat end 106, a body portion 107, a generally arcuate, serrated portion 108, and a through-hole 109. Preferably, serrations on serrated portion 108 are disposed about a circular path of about 180°. A through-slot 110 is disposed in body 107 proximate flat end 106, and receives a threaded distractor nut 112, as shown in FIG. 1. Distractor bar 18 is disposed about a distractor axis 114, and when axis 114 coincides with axis 116 of adjustable fixator 10, end 106 may be inserted into blind hole 38 of distractor body 12. The cross-section of body portion 107 of distractor bar 18 is keyed, as shown in FIG. 4C, with an arcuate section 118 and a flat section 120. Blind hole 38 of distractor body 12 serves as a keyway for receiving body portion 107. Thus, one preferred orientation of distractor bar 18 may be set with respect to distractor body 12 as well as distractor clamp assembly 14. It can be appreciated that the keyway and through-hole may take other shapes to provide a desired orientation, to prevent rotation, or both.

A hole 122 is provided in distractor bar 18, and is disposed centrally about distractor axis 114. Hole 122 is sized to receive threaded body 45 of distractor screw 44. Preferably, threaded body 45 is threadably associated with threaded distractor nut 112. Alternatively, or in addition thereto, threading may be provided in hole 122 of distractor bar 18. Thus, because distractor screw 44 is held in a fixed position with respect to distractor body 12, turning of distractor screw 44 about coincident axes 39, 114, 116 results in either an increase or decrease in the overall length of an assembled distractor body 12 and distractor bar 18. Such length adjustments thus permit distraction or compression of bone segments to be achieved using fixator 10. Desired length adjustments may be measured, for example, using a scale 124 provided on a side of distractor bar 18, for example a flat 126a, as shown in FIGS. 1 and 4C.

Referring to FIG. 2, in order to prevent over-extension of distractor screw 44 and inadvertent disassembly, an unthreaded gap 45a may be provided along threaded body 45 near threaded end portion 52b. In one exemplary embodiment, a gap 45a larger than the width of distractor nut 112 and sized to about 5 mm is provided, in which region the diameter of body 45 is smaller than at threaded regions. Further translation of distractor screw 44 with respect to distractor nut 112 thus can be avoided when gap 45a reaches distractor nut 112. Because unthreaded gap 45a is not disposed at a free end of distractor screw 44, travel of distractor body 12 with respect to distractor body 18 may be interrupted yet distractor body 12 does not become detached from distractor body 18.

Figure 5B:
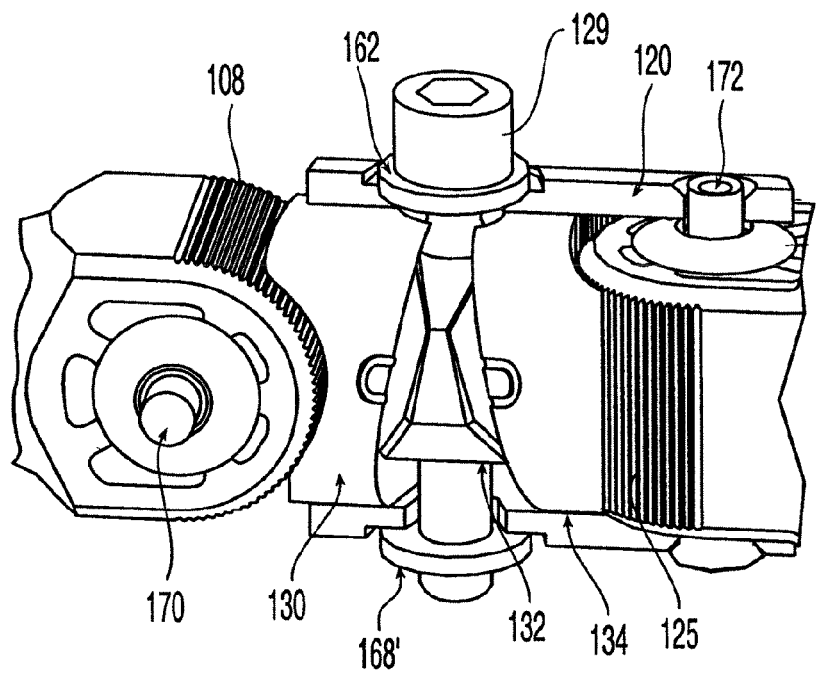
FIGS. 5B-5C show partial cross-sectional perspective views of the first body portion of FIG. 5 without o-rings being shown.
Figure 5C:
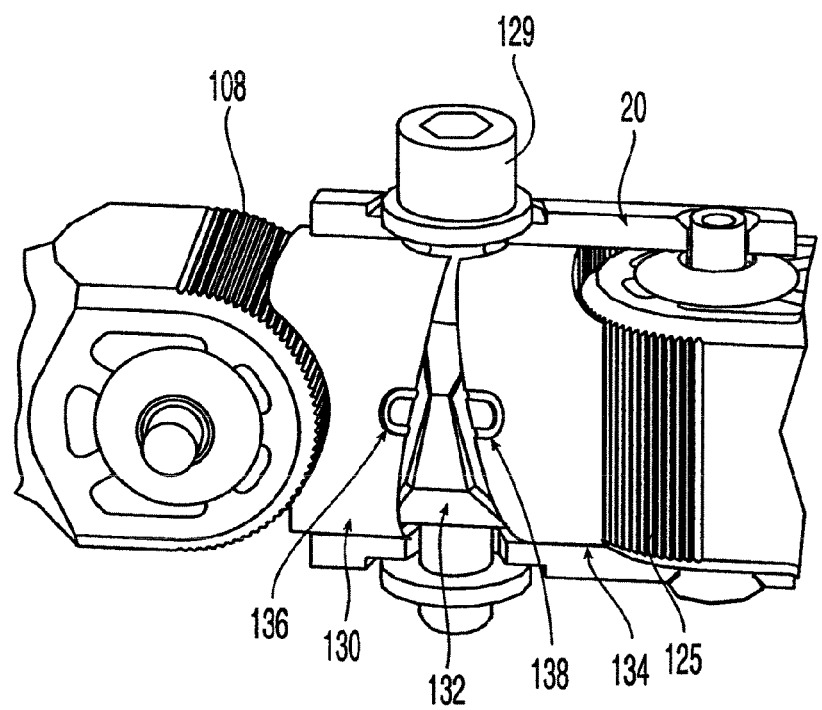
Figure 5H:
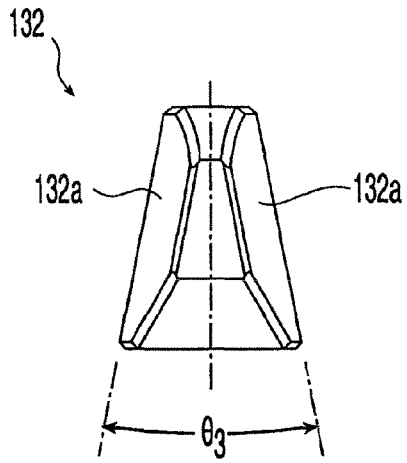
FIG. 5H shows a side view of the wedge actuator of FIG. 5.
Figure 5I:
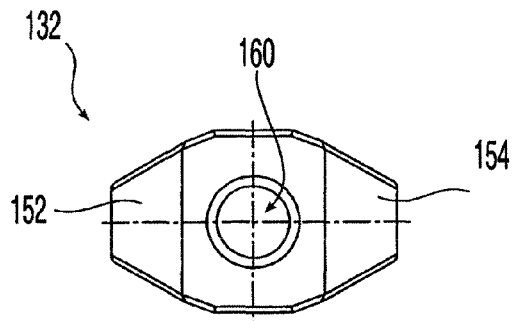
FIG. 5I shows a bottom view of the wedge actuator of FIG. 5.
Figure 5J:
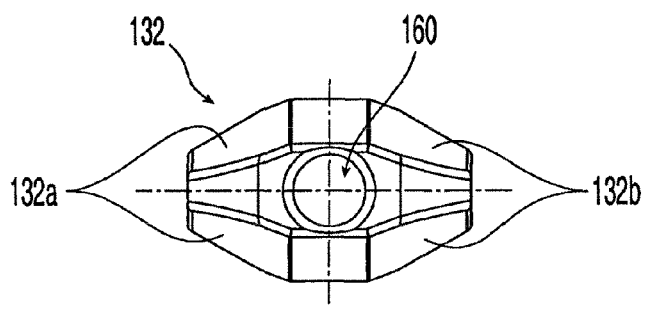
FIG. 5J shows a top view of the wedge actuator of FIG. 5.
Figure 5K:
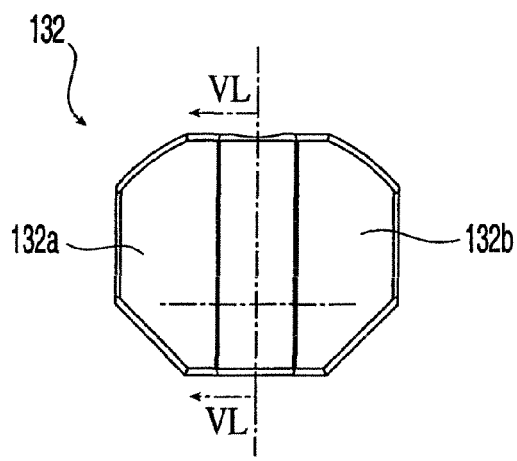
FIG. 5K shows a front view of the wedge actuator of FIG. 5.
Figure 5L:
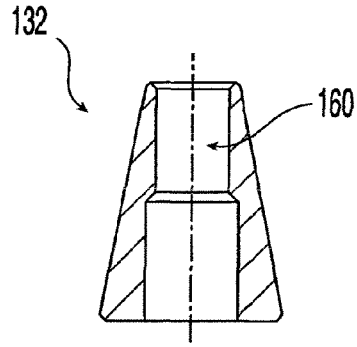
FIG. 5L shows a cross-sectional view along line VL-VL of the wedge actuator of FIG. 5H.

Referring to FIGS. 5-5C, and as discussed earlier with respect to FIG. 1, first body portion 16 includes a distractor bar 18, distractor joint assembly 20, and coupling 22 with integral serrated portion 125. These components are shown aligned with axes 39, 114, 116. Joint assembly 20 is configured to permit swivelling or articulation of distractor bar 18 and coupling 22 about generally perpendicular axes 126, 128, respectively. In addition, joint assembly 20 is configured to permit releasable locking of such articulation of distractor bar 18 and coupling 22, simultaneously, using joint lock screw 129 as will be explained below. Thus, releasable locking may be achieved simultaneously in two degrees of freedom. To this end, housed in joint assembly body 20a of joint assembly 20 are a first lock piece 130, a wedge actuator 132, and a second lock piece 134, an exemplary assembled configuration of which is shown in partial cross-section in FIGS. 5B-5C.

A side view of first lock piece 130 is shown in FIG. 5D, while a cross-section is shown in FIG. 5E. Similarly, side and cross-sectional views of second lock piece 134 are shown in FIGS. 5F and 5G. As evident from the side views of FIGS. 5D and 5F, lock pieces 130, 134 have arcuate side walls 131, 135, respectively. In one exemplary embodiment, lock piece 130 has two arcuate recesses 136 on side wall 131, while lock piece 134 has two arcuate recesses 138 on side wall 135. As shown in FIGS. 5 and 5C, each pair of opposed recesses 136, 138 is sized to receive a resilient o-ring 139, which seats in the recesses and provides limited biasing of lock pieces 130, 134 toward each other. In an alternate embodiment, a tension spring could be used in place of o-ring 139. Preferably, upper recesses 140, 142 are provided in lock pieces 130, 134, respectively, to receive a portion of joint lock screw 129, just below the head thereof. Serrated portion 108 of distractor bar 18 engages serrated portion 144 of first lock piece 130, while serrated portion 125 of coupling 22 engages serrated portion 146 of second lock piece 134.

Lock pieces 130, 134 are configured to slidingly engage wedge actuator 132. In an exemplary embodiment, inner surfaces 148, 150 of lock pieces 130, 134 are disposed in transverse planes at an angle of about 22° with respect to each other. As shown in FIGS. 5E and 5G, inner surface 148 preferably may be oriented at an angle $\theta_1$ with respect to a line perpendicular to bottom face 149 of first lock piece 130, and inner surface 150 preferably may be oriented at an angle $\theta_2$ with respect to a line perpendicular to bottom face 151 of second lock piece 134. Angles $\theta_1, \theta_2$ are preferably about the same, each preferably between about 5° and about 35°, and more preferably about 11°. Inner surfaces 148, 150 serve as contact surfaces upon which wedge actuator 132 slides. Turning to FIGS. 5H-5L, wedge actuator 132 includes a pair of outer surfaces 152, 154 disposed in transverse planes, such that outer surfaces 152, 154 are disposed at an angle $\theta_3$ with respect to each other. Preferably, angle $\theta_3$ is about twice the amount of angles $\theta_1$ or $\theta_2$, and between about 10° and about 70°, and more preferably about 22°. Inner surfaces 148, 150 of lock pieces 130, 134 may each slidingly engage one of the outer contact surfaces 132a, 132b of wedge actuator 132.

Figure 5M:
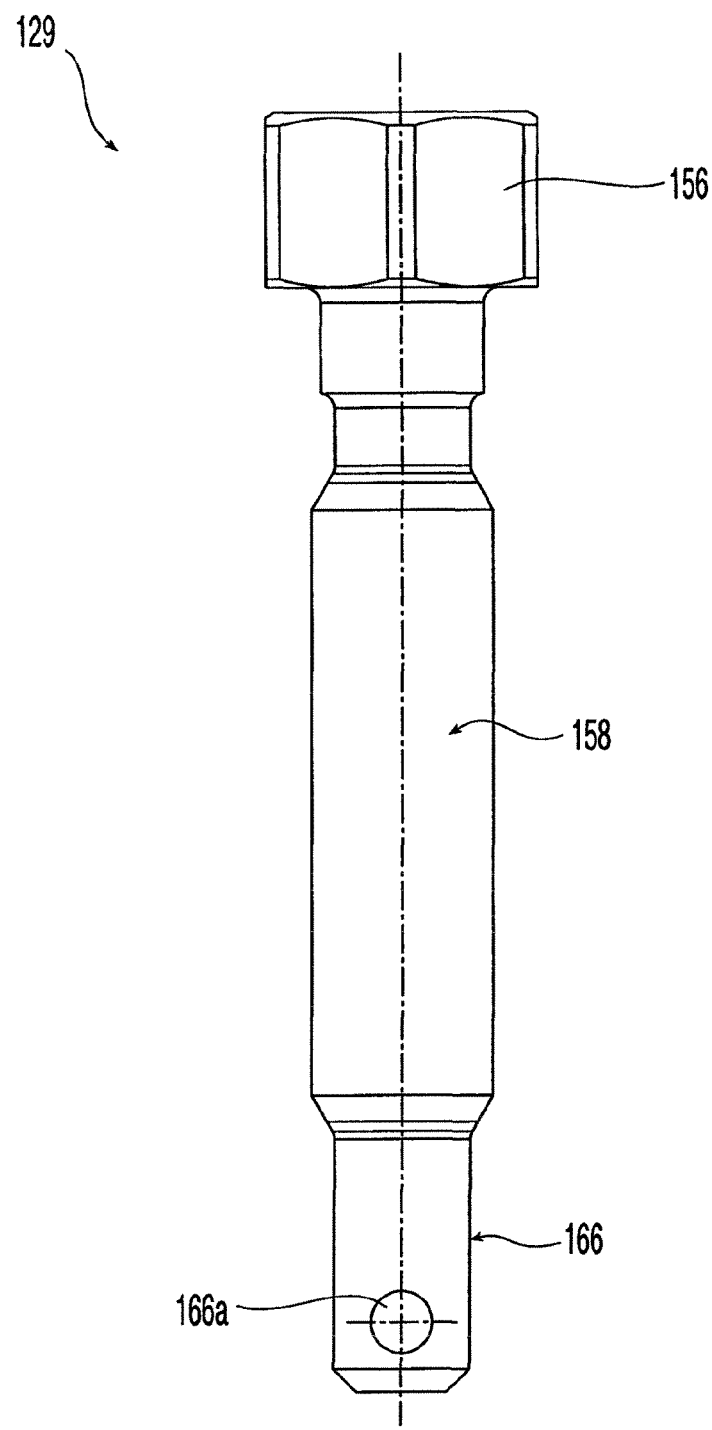
FIG. 5M shows a side view of the joint lock screw of FIG. 1.

The position of wedge actuator 132 between first and second lock pieces 130, 134 is adjustable using joint lock screw 129, shown in FIG. 5M. Joint lock screw 129 has a head 156 and a threaded shaft 158. Preferably, head 156 includes a hexagonal or other shaped region that may be engaged by a suitably shaped tool, such as a hexagonal key. Preferably, the shaped region is recessed but the outer surface of the head 156 may itself be shaped to engage a tool. Shaft 158 preferably threadably engages a threaded hole 160 in wedge actuator 132. When fully assembled, head 156 preferably abuts a washer 162 that rests in a corresponding recess 164 in joint assembly body 20a of joint assembly 20. Lower portion 166 of joint lock screw 129 protrudes from an opposite side of joint assembly body 20a, and is fixed in place by a cap 168. Lower portion 166 of joint lock screw 129 includes a through hole 166a disposed transverse to the longitudinal axis of shaft 158, and cap 168 similarly includes a through hole 168a so that when cap 168 is disposed on joint lock screw 129, through hole 166a may be aligned with through hole 168a. Once aligned, a pin 168b may be inserted therein, preferably with an interference fit, to couple cap 168 and joint lock screw 129. In an alternate embodiment, lock screw 129 is fixed in place by a retaining ring coupled to lower portion 166 at a groove therein. Optionally, a washer 168' may be provided between the retaining ring and joint assembly body 20a (shown for example in FIGS. 5B and 5C).

An exemplary embodiment of joint assembly body 20a of joint assembly 20 is shown in FIGS. 5N-5Q. As shown in FIG. 5O, joint assembly body 20a preferably has a generally circular cross-section, adapted to receive lock pieces 130, 134 with similar arcuate outer walls. Referring again to FIG. 5A, lock pieces 130, 134 are retained within joint assembly 20 using joint pivot pins 170, 172. Pin 170 couples distractor bar 18 to joint assembly body 20a, and is received in coaxial holes 174 of joint assembly body 20a and through-hole 109 of distractor bar 18. Similarly, pin 172 couples the coupling 22 to joint assembly body 20a, and is received in coaxial holes 176 of joint assembly body 20a and through-hole 178 of coupling 22.

In operation, joint lock screw 129 preferably may be threadably associated with threaded hole 160 in wedge actuator 132. Because lock screw 129 is positionally fixed by cap 168, although rotatable about its central axis 180, threadable engagement of lock screw 129 with wedge actuator 132 results in upward or downward travel of wedge actuator 132 with respect to head 156 of lock screw 129, along central axis 180. During upward movement, outer contact surface 132a of wedge actuator 132 slidingly engages inner surface 148 of lock piece 130, and outer contact surface 132b of wedge actuator 132 slidingly engages inner surface 150 of lock piece 134, so that serrated portions 144, 146 of lock pieces 130, 134 are engaged with serrated portion 108 of distractor bar 18 and serrated portion 125 of coupling 22 to releasably lock the components in place. Thus, the angulation of distractor bar 18 about axis 126 as well as the angulation of coupling 22 about axis 128 may be releasably fixed. Downward movement of wedge actuator 132 simultaneously releases pressure between the mutually engaging serrated surfaces of lock pieces 130, 134, distractor bar 18, and coupling 22, so that distractor bar 18 and coupling 20 of fixator 10 may be readily angulated with respect to each other.

While the embodiment shown and described herein has the ability to lock rotation or articulation of components about generally perpendicular axes, in other embodiments the axes need not be perpendicular. For example, a wedge actuator 132 may be disposed between a pair of lock pieces 130, so that the serrations of the lock pieces and the direction of articulation are about the same on either side of wedge actuator 132. Alternatively, a pair of lock pieces 134 may be used. Thus, the pair of components such as distractor bar 18 and coupling 22 may be oriented within the same plane. In yet other embodiments, the axes defining articulation of the two components may be transverse to each other, so that the components may be oriented in transverse planes.

Referring next to FIGS. 1 and 6A-6C, central joint assembly 24 is shown having a joint 24a with a borehole 182 extending therethrough along a borehole axis 184. Borehole 182 is configured and dimensioned for receiving opposing couplings 22, 28, as will be described shortly. In one exemplary embodiment, joint 24a of central joint assembly 24 includes a slit 186 from side surface 188 to borehole surface 190, and which extends the length of joint 24a to define assembly portions 192, 194. A fastener hole 196 is also included, and extends from side surface 198 to side surface 199, through assembly portions 192, 194. A threaded center clamp screw 200, preferably seated on a spherical washer 202, extends through fastener hole 196, and threadably engages a stainless steel threading insert 204 disposed in fastener hole 196 proximate side surface 198. Spherical washer 202 preferably is seated in a spherical recess in joint 24a of central clamp assembly 24 proximate side surface 199.

The spherical geometry of the washer and recess aid in the clamping action of center clamp screw 200. In an alternate embodiment, fastener hole 196 may be threaded between connecting assembly portion 194 and side surface 198.

Figure 6A:
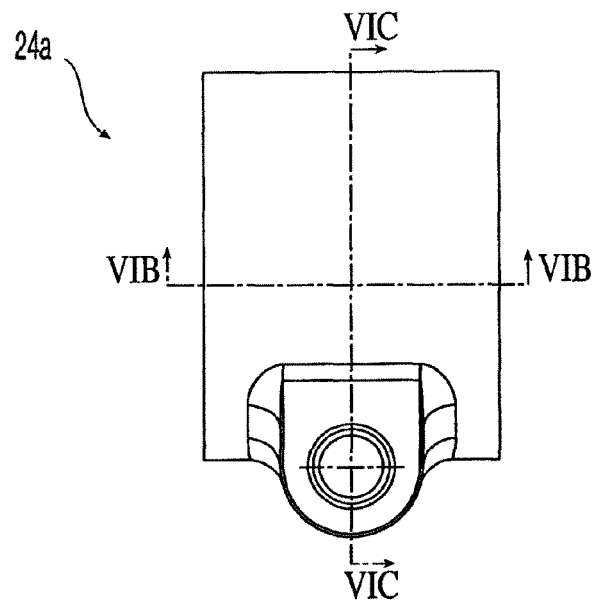
FIG. 6A shows a side view of the joint of the central clamp assembly of FIG. 1.
Figure 6B:
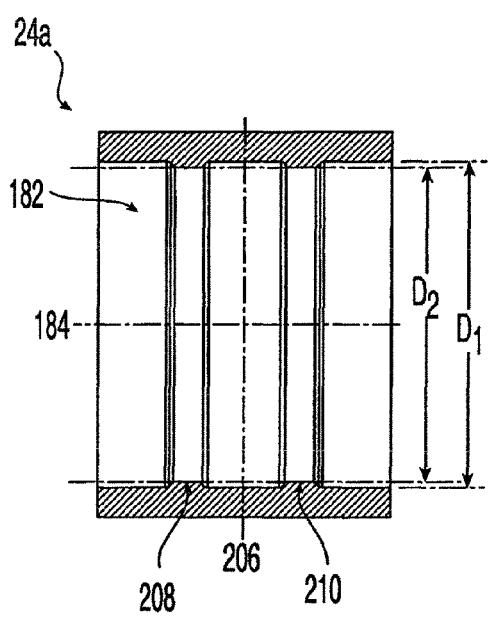
FIGS. 6B and 6C show cross-sectional views of the joint of the central clamp assembly of FIG. 6A along line VIB-VIB and VIC-VIC, respectively.
Figure 6C:
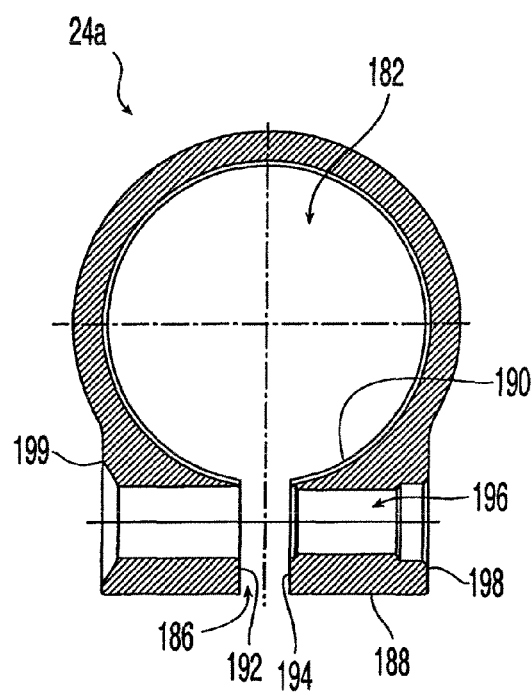

As shown particularly in FIG. 6B, borehole 182 of joint 24a of central joint assembly 24 is generally symmetrical about a plane through center axis 206, which plane is perpendicular to borehole axis 184. Borehole 182 generally has an inner diameter $D_1$, but includes circumferential inner ribs 208, 210 which form an inner diameter $D_2$ that is smaller than diameter $D_1$.

Figure 7A:
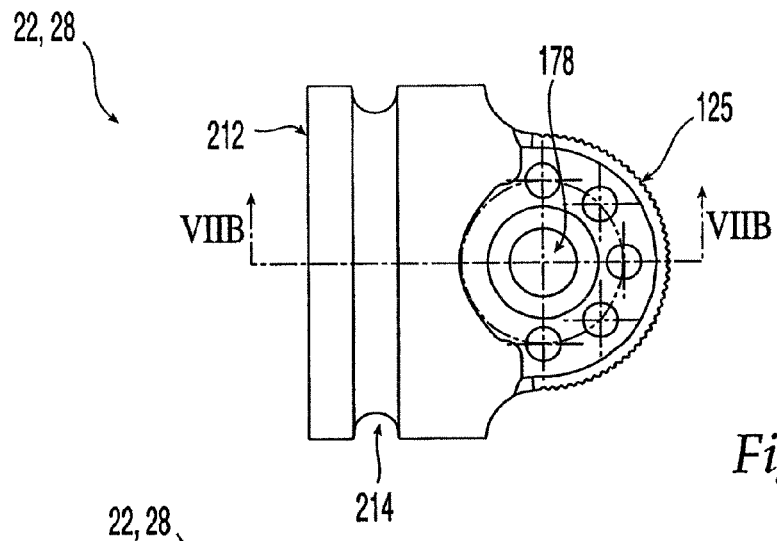
FIG. 7A shows a side view of the coupling of FIG. 1.
Figure 7B:
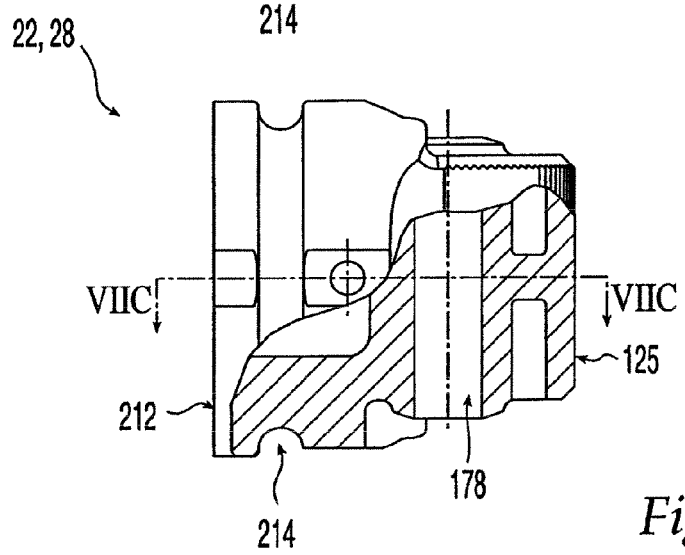
FIG. 7B shows a cross-sectional view of the coupling of FIG. 7A along line VIIB-VIIB.
Figure 7C:
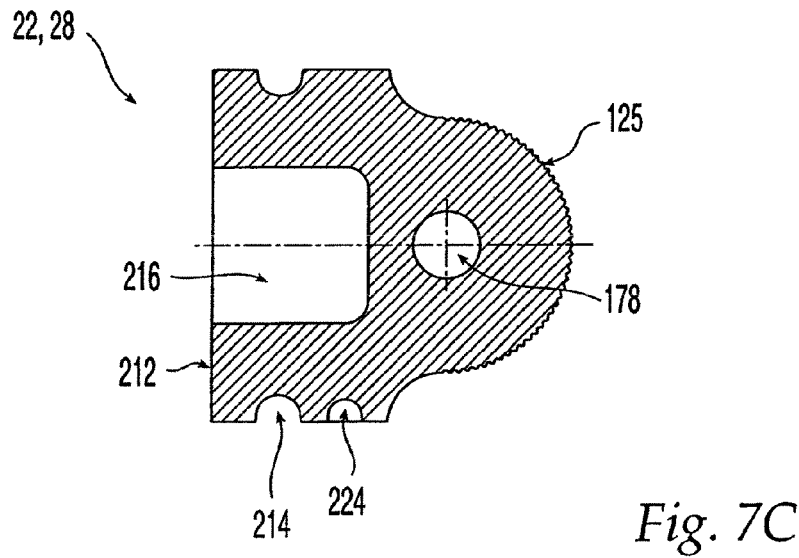
FIG. 7C shows a cross-sectional view of the coupling of FIG. 7A along line VIIC-VIIC.
Figure 8A:
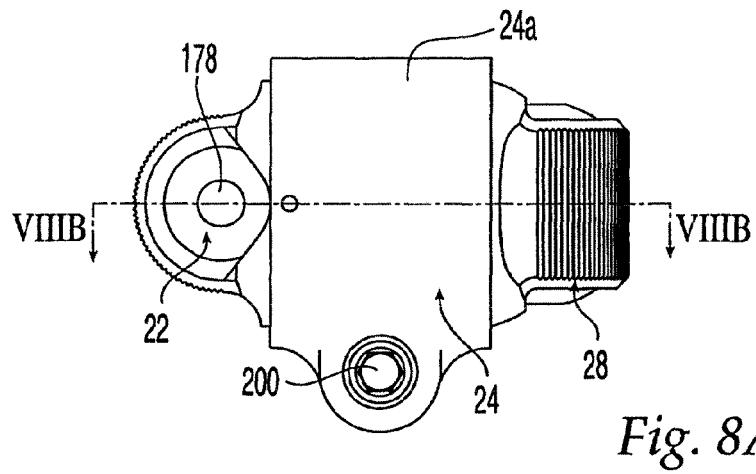
FIG. 8A shows the central clamp assembly of FIG. 6A with a pair of couplings inserted therein.
Figure 8B:
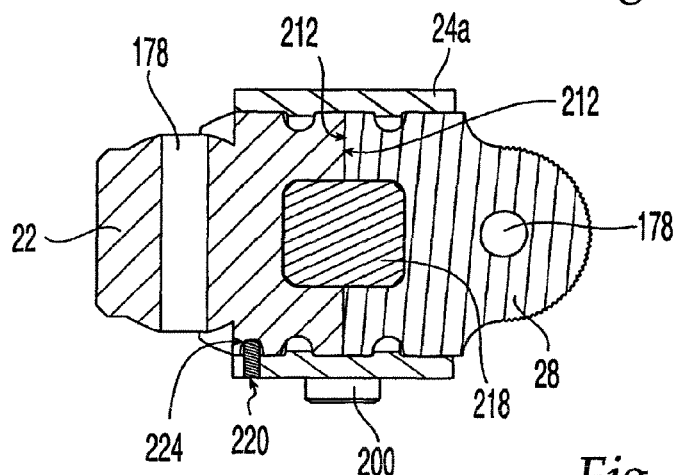
FIG. 8B shows a cross-sectional view of the assembled central clamp assembly of FIG. 8A along line VIIIB-VIIIB.
Figure 8C:
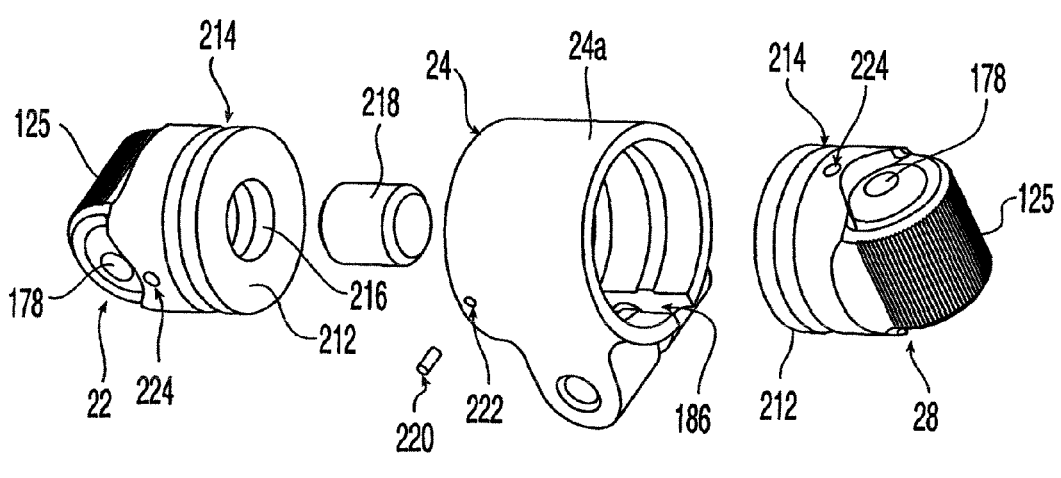
FIG. 8C shows an exploded perspective view of the assembled central clamp assembly of FIG. 8A.

Couplings 22, 28 are configured and dimensioned to be received in borehole 182 and releasably rotate therein. Turning to FIGS. 7A-7C, each coupling 22, 28 includes an integral serrated portion 125 and a flat face 212. A circumferential groove 214 is sized to receive one of the ribs 208, 210 in borehole 182 and rotate about borehole axis 184. Alternatively, one of the couplings 22, 28 may be formed with a recess 216 and the other coupling may be formed with a projection which fits into and corresponds with recess 216. In addition, a hollow portion 216 may be provided. In some embodiments, as shown in FIGS. 8A-8C, a central support piece 218 is disposed in hollow portions 216 between couplings 22, 28 to provide increased stiffness along borehole axis 184. In one exemplary embodiment, one coupling 22, 28 may be retained in borehole 182 with a set screw or pin 220, which extends through a hole 222 in joint 24a of central joint assembly 24 and is received in a recess 224 in the coupling 22, 28. The set screw or pin 220 may permit one coupling 22, 28 to be rotationally fixed with respect to central joint assembly 24, while the other coupling 22, 28 may freely rotate. Thus, access to center clamp screw 200 may be permitted while a coupling 22, 28 is rotated. When slit 186 is generally open, as shown for example in FIG. 6C, couplings 22, 28 are free to slidably rotate in borehole 182. When a desired orientation of couplings 22, 28 has been chosen about rotational axis 184, screw 200 may be tightened, thereby decreasing the separation of regions 192, 194 of joint 24a and arresting rotation of couplings 22, 28. Preferably, the rotation of each coupling 22, 28 is simultaneously governed by the degree of tightening of screw 200; thus, both couplings 22, 28 either are free to rotate or fixed in position.

In an alternate embodiment, borehole 182 of joint 24a of central joint assembly 24 may be smooth, without inner ribs 208, 210. A pair of set screws or pins 220 may be received in suitable holes in central joint assembly 24. One screw or pin 220 may be received in a recess 224 in each coupling 22, 28 such that couplings 22, 28 may be retained in borehole 182.

As shown in FIGS. 9A to 9C, second body portion 26 includes a coupling 28, a T-clamp joint assembly 30, and a T-clamp link 32. T-clamp joint assembly 30 of second body portion 26 is the same as distractor joint assembly 20, which was previously described with respect to FIGS. 5B to 5Q, and thus is not described again in detail. However, it should be noted that second body portion 26 is configured to permit swivelling or articulation of coupling 28 and T-clamp link 32 about generally perpendicular axes 226, 228, respectively. When second body portion 26 is aligned about axis 116 of adjustable fixator 10, as shown for example in FIG. 1, axis 226 is parallel to axis 126 of distractor joint assembly 20, while axis 228 is parallel to axis 128 of assembly 20. However, these axes may be non-parallel as a result of the articulation permitted by first body portion 16, central joint assembly 24, and second body portion 26.

With reference to FIGS. 9A to 9C, T-clamp link 32 is provided with serrations on a serrated portion 230 that are disposed about a circular path of about 180°. Serrated portion 230 of T-clamp link 32 engages with serrated portion 146 of lock piece 134 so that T-clamp link 32 may be releasably locked in place. A pin 172 couples T-clamp link 32 to joint assembly body 20a of T-clamp joint assembly 30, and is received in coaxial holes 176 of joint assembly body 20a and a through-hole 232 of link 32. T-clamp link 32 is further provided with a body portion 234 and a pair of extensions 236, 238 with coaxial holes 240 disposed on an axis 242. Preferably, axes 228, 242 are parallel. Extensions 236, 238 define a central opening 244 that preferably is disposed symmetrically about link central axis 246, and is sized to accommodate T-clamp pivot 36 as will be described. A pair of pin holes 248, 250 are also provided in extensions 236, 238, and are preferably disposed perpendicular to hole 240. As shown in FIG. 1, a T-clamp pivot pin 252 is inserted in holes 240, and secured to extensions 236, 238 by cross pins 254 that fit in pin holes 248, 250 as well as like positioned holes in pivot pin 252. An interference fit may be used between portions of cross pins 254 and pin holes 248, 250 to retain cross pins 254 therein. Preferably, T-clamp pivot pin 252 is rotationally fixed with respect to T-clamp link 32.

Turning to FIG. 10A, T-clamp assembly 34 is shown with opposing front vise plate 256 and rear vise plate 258 each having grooves 259 for receiving bone fasteners. Plates 256, 258 are connected with a T-clamp lock screw 260, as shown in FIG. 1. Lock screw 260 projects through holes 280, 282 in plates 256, 258, respectively, which are coupled together with a pair of vise screws 68 each having a vise washer 70. Vise screws 68 extend through holes 262, 264, within respective compression springs 76, and preferably may be threadably received in holes 266, 268 in rear vise plate 258. Thus, it should be noted that until vise plates 256, 258 of T-clamp assembly 34 are tightened with respect to each other, springs 76 bias vise plates 256, 258 away from each other while permitting vise plates 256, 258 generally to be disposed in either parallel or non-parallel planes as a function of the degree of tightening of each vise screw 68. The upper and lower ends of springs 76 also may abut recessed regions in vise plates 256, 258. Rear vise plate 258 also is provided with a pair of holes 270, 272 through which clamp attachment screws 274a extend. As shown in FIGS. 1 and 10B to 10D, T-clamp pivot 36 includes a pair of outer holes 274, 276 which are disposed such that attachment screws 274a may be received therein. A central hole 278 in T-clamp pivot 36 may be disposed coaxially with holes 280, 282 in vise plates 256, 258, respectively, and holes 278, 280, 282 receive T-clamp lock screw 260. Lastly, a through hole 284 is disposed in extension 286 of T-clamp pivot 36, and preferably runs perpendicular to hole 278. The hole 278 includes a threaded portion 278a and an unthreaded counterbore portion 278b, with the diameter of counterbore 278b being larger than the diameter of threaded portion 278a.

T-clamp pivot 36 is coupled to T-clamp link 32 when T-clamp pivot pin 252 extends through coaxial holes 240, 284. A hexagonal or other shaped region, preferably a recessed region, may be provided in upper end 260a of lock screw 260, and may be engaged by a suitably shaped tool, such as a hexagonal key. Lock screw 260 preferably has a threaded shank 260b which is threadably associated with threaded portion 278a of hole 278 in T-clamp pivot 36. To arrest pivoting of T-clamp assembly 34 about T-clamp pivot pin 252, in one exemplary embodiment, T-clamp lock screw 260 may be positioned so that lower end 260c of T-clamp lock screw 260 bears against T-clamp pivot pin 252. The body of T-clamp pivot pin 252 may be generally hexagonal such that flats are included along the body to provide more surface area for lower end 260c of T-clamp lock screw 260 to bear against.

Lower end 260c of T-clamp lock screw 260 (shown in FIG. 1) forms a shoulder that abuts the shoulder formed at the intersection of portions 278a, 278b of hole 278 in T-clamp pivot 36 (shown in FIG. 10D), thereby limiting travel of T-clamp lock screw 260.

Other embodiments of clamp assembly 14 and/or T-clamp assembly 34 also may be employed. For example, T-clamp pivot 36 may be integrally formed with lower vise plate 258, obviating the need for attachment screws 274a extending through holes 270, 272.

In an exemplary embodiment, distractor body 12, distractor bar 18, couplings 22, 28, T-clamp link 32, and lock pieces 130, 134 are formed of a polymer such as Victrex® 450CA30, a radiolucent carbon fiber reinforced polyaryletherketone thermoplastic which can withstand many autoclave sterilization cycles and concomitantly possesses high mechanical strength, resistance to stress cracking, as well as chemical resistance. The radiolucent properties of this polymer advantageously permit visualization of underlying bones and/or joints when fixator 10 is disposed in the field of view of x-ray equipment, thus for example permitting imaging of the anatomic alignment of bones and/or the surfaces of joints proximate the fixator. This polymer also is chosen for its relatively light weight. Preferably, T-clamp link 32 is formed of a radiolucent polymer so that shadows are avoided in imaging. Advantageously, when the fixator of the present invention is used in connection with the treatment of badly comminuted distal tibia fractures, otherwise known as pilon fractures, the radiolucent T-clamp link permits suitable joint visualization.

Preferably, body joints 20a of distractor joint assembly 20 and T-clamp joint assembly 30, as well as joint 24a of central joint assembly 24, are formed of 6061-T6 aluminum, which provides radiolucent characteristics when suitably thin. Vise plates 56, 58, 256, 258 and T-clamp pivot 36 are formed of titanium alloy (Ti-6% Al-4% V), and wedge actuator 132 is preferably formed of 17-4 PH hardened stainless steel. In an alternate embodiment, wedge actuator 132 is formed of 316L stainless steel. Other fasteners or fastener-like components disclosed herein, such as joint lock screw 129, preferably may be metallic and may be formed of a material of suitable hardness such as 17-4 PH hardened stainless steel or 316L stainless steel. Fasteners may also be provided with a surface coating of electroless nickel with phosphorous that is co-deposited with polytetrafluoroethylene (PTFE), as available for example from Anoplate Corporation, Syracuse, N.Y. Such a surface coating provides resistance to galling, and also provides lubrication. Alternatively, the fasteners or fastener-like components may be formed of a material that resists galling such as gall tough stainless steel.

Thus, to summarize the articulation provided by adjustable fixator 10, distractor joint assembly 20 permits angulation of components about two preferably perpendicular axes, central joint assembly 24 permits rotation of components about two preferably parallel planes, T-clamp joint assembly 30 permits angulation of components about two preferably perpendicular axes, and T-clamp pivot 36 permits angulation about an additional axis. Furthermore, the overall length of adjustable fixator 10 may be grossly adjusted, and the position of distractor clamp assembly 14 may be adjusted relative to distractor body 12. Fine length adjustments, for example to achieve compression and distraction, may be accomplished using distractor screw 44.

Figure 11:
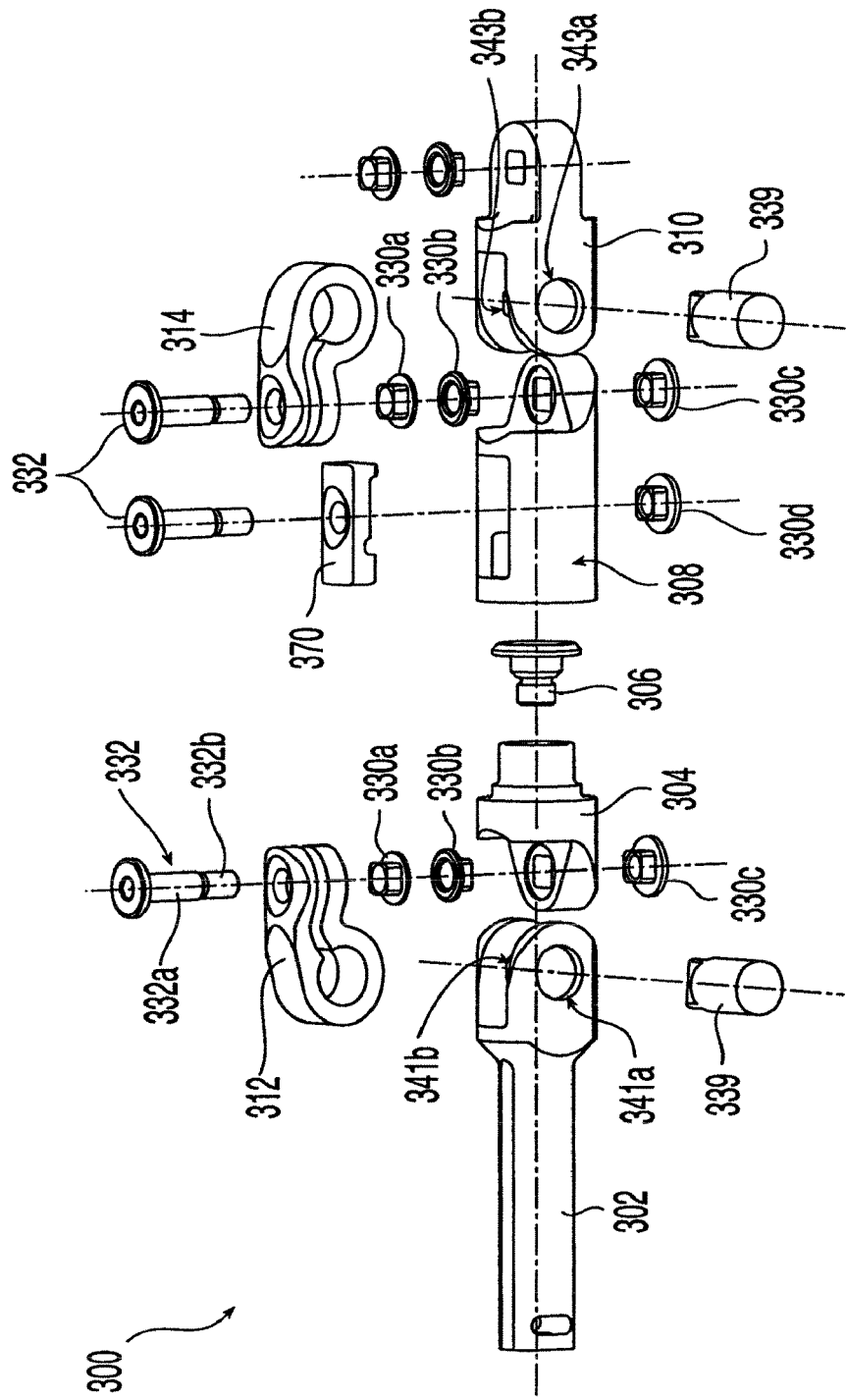
FIG. 11 shows an exploded view of another embodiment of a joint assembly for use with an apparatus for the external fixation of bones.

Turning now to FIG. 11, an alternate arrangement of joints is shown for use in an external fixator. Joint assembly 300 includes a distractor rod 302, a first rotatable segment 304, a rotatable segment cap or swivel segment 306, a second rotatable segment 308, and a T-clamp link 310. Clamp assemblies suitable for holding bone pins may be secured at either end of joint assembly 300. A tension clamp 312 couples distractor rod 302 to first rotatable segment 304, and another tension clamp 314 couples second rotatable segment 308 to T-clamp link 310. As shown in FIG. 11, tension clamps 312, 314 are mirror images of each other. Thus, while tension clamp 312 will be discussed in detail, the discussion applies to tension clamp 314 as well.

Figure 12A:
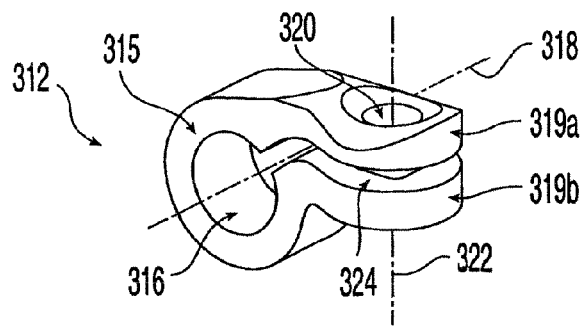
FIG. 12A shows a perspective view of a tension clamp of FIG. 11.
Figure 12B:
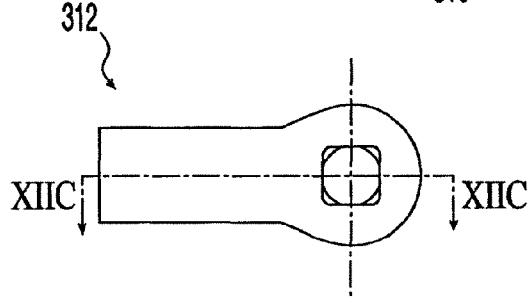
FIG. 12B shows a side view of the tension clamp of FIG. 12A.
Figure 12C:
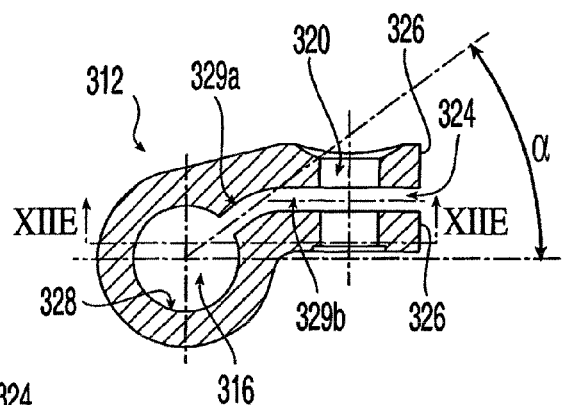
FIG. 12C shows a cross-sectional view along line XIIC-XIIC of the tension clamp of FIG. 12A.
Figure 12D:
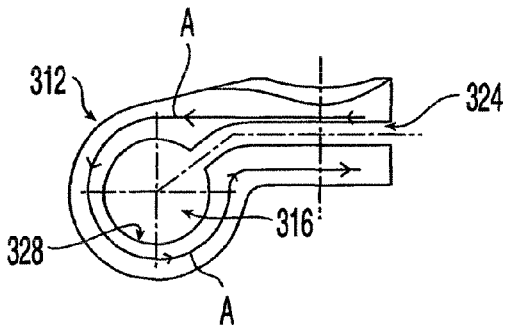
FIG. 12D shows the direction of fiber reinforcement of the tension clamp of FIG. 12A.
Figure 12E:
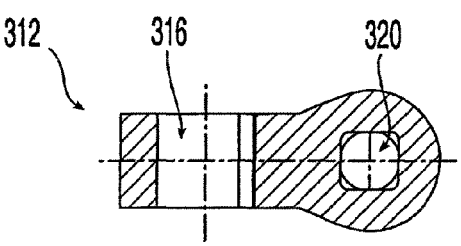
FIG. 12E shows a cross-sectional view of the tension clamp of FIG. 12C along line XIIE-XIIE.
Figure 12F:
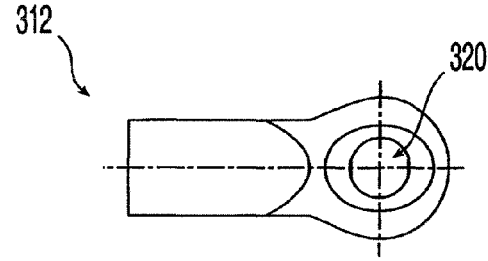
FIG. 12F shows a top view of the tension clamp of FIG. 12A.
Figure 13A:
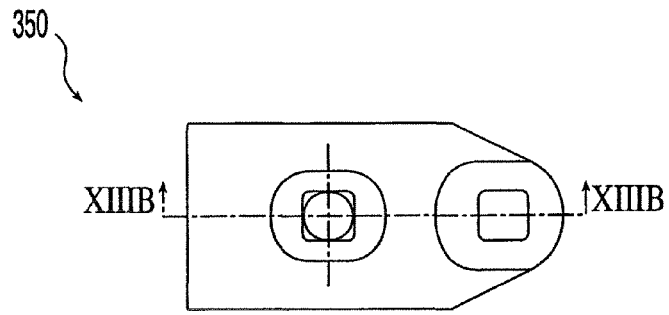
FIG. 13A shows a bottom view of the main body of FIG. 11.
Figure 13B:
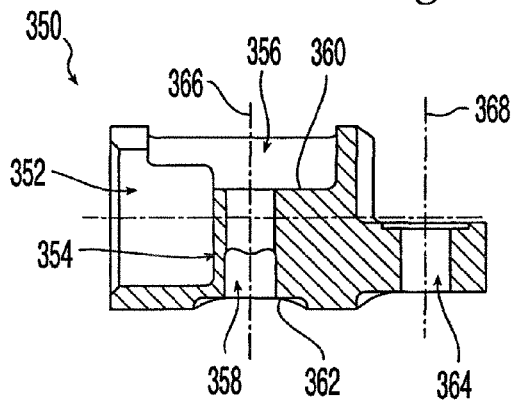
FIG. 13B shows a cross-sectional view of the main body of FIG. 13A along line XIIIB-XIIIB.
Figure 13C:
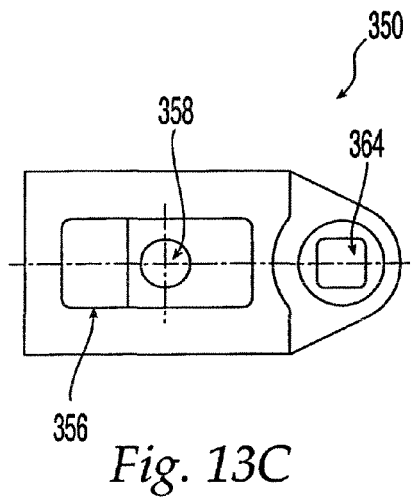
FIG. 13C shows a top view of the main body of FIG. 13A.
Figure 13D:
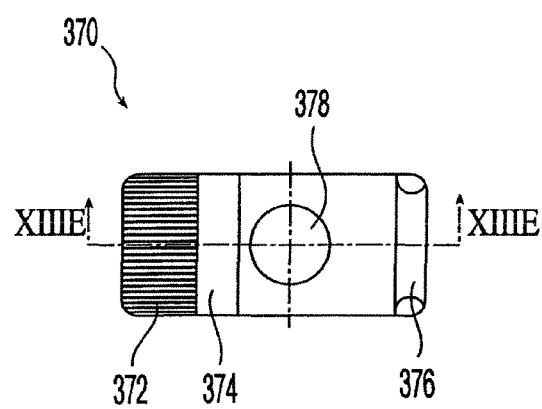
FIG. 13D shows a bottom view of the cover of FIG. 11.
Figure 13E:
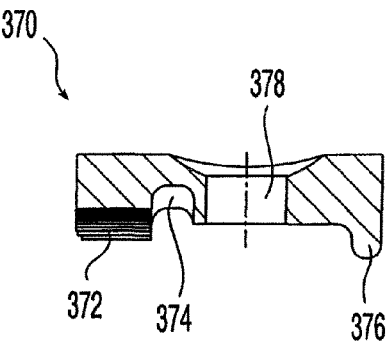
FIG. 13E shows a cross-sectional view of the cover of FIG. 13D along line XIIIE-XIIIE.

Referring to FIGS. 12A to 12F, tension clamp 312 includes a generally cylindrical body portion 315 with a first through hole 316 disposed along a first central hole axis 318. A pair of generally parallel extensions 319a, 319b are connected to body portion 315, and include a second through hole 320 that is disposed along a second central hole axis 322. Preferably axes 318, 322 are generally perpendicular to each other. Extensions 319a, 319b are biased apart, separated by a slit 324 which extends from side surfaces 326 to through hole surface 328 and the width of tension clamp 312. Slit 324 preferably includes first and second sections 329a, 329b, respectively, that are oriented at an angle α with respect to each other. In one exemplary embodiment, angle α is between about 20° and 50°, and more preferably about 33.6°. As shown in FIG. 12D, fiber reinforcement preferably may be provided along the direction of arrows A. Preferably, as shown in FIG. 11, an insert nut 330a may be seated in through hole 320 and receives a fastener 332 with a smooth upper portion 332a and threaded lower portion 332b. Each fastener 332 preferably includes a head with a spherical lower portion for mating in a spherical recess. In one embodiment shown in FIG. 12G, insert nut 330a has a circular head 334, a non-circular body 336, and a central through-hole 337. Non-circular body 336, for example, may be square-shaped or any other suitable shape. Preferably, the seat in through-hole 320 has a similarly non-circular shape so that insert nut 330a does not freely rotate therein. Insert nut 330a additionally may be adhesively bonded to body 336.

First rotatable segment 304 is provided with a through hole 340 into which opposing insert nuts 330b and 330c are seated. Preferably, as described with respect to insert nut 330a, seats in through hole 340 are shaped so that when insert nuts 330b,330c are inserted therein, rotation is prevented. Preferably, the upper surface 338 of head 334 of insert nuts 334a, 334b is serrated, such as with a star-grind pattern, so that when the heads 334 of insert nuts 334a,334b abut each other, the serrated surfaces on the heads frictionally mate and may rotate with respect to each other about substantially regularly spaced engaging serrations.

Thus, when heads 334 of opposing insert nuts 334a,334b are loosely disposed with respect to each other, the heads are free to rotate with respect to each other, whereas when heads 334 are pressed firmly against each other, rotational movement is arrested. First rotatable segment 304 further may include a recessed region 342, so that when the body 336 of an insert nut 330b is disposed in hole 340, head 334 substantially fits within recessed region 342. In an exemplary embodiment, the through-hole 337 in insert nuts 330a,330b is smooth, while through-holes 337 in insert nuts 330c are threaded to receive threaded lower portions 332b of fasteners 332.

When assembled, a yoke pin 339 is received in coaxial holes 316, 341a, 341b of distractor rod 302. In an exemplary embodiment, yoke pin 339 is keyed so that it does not rotate with respect to distractor rod 302. Thus, a tension clamp 312 couples distractor rod 302 to first rotatable segment 304. Similarly, another non-rotating yoke pin 339 is received in coaxial holes 316, 343a, 343b of T-clamp link 310, and tension clamp 314 couples second rotatable segment 308 to T-clamp link 310.

Thus, when a desired orientation of distractor rod 302 or T-clamp link 310 has been chosen, the fastener 332 may be tightened by threadably engaging fastener 332 with insert nut 330c, thereby decreasing the diameter of through hole 316 and decreasing the separation of extensions 319a, 319b, so that articulation is arrested. Preferably, the articulations about axes 318, 322 is simultaneously governed by the degree of tightening of fastener 332; thus, for example, distractor bar 302 either freely rotates about both axes 318, 322 or it is fixed in position.

Swivel segment 306, shown in cross-section in FIG. 12J, includes a first cylindrical end 344, a second cylindrical portion 345, and a third circular end 346. The diameter of end 346 is larger than the diameter of portion 345 which is larger than the diameter of end 344. In one exemplary embodiment of first rotatable segment 304, a hole 348 is provided, and is configured and dimensioned to receive end 344 and portion 345 of swivel segment 306, which may be fixed therein. End 344 preferably is threadably received in hole 348. In an alternate embodiment, swivel segment 306 is rotatably retained or integrally provided in first rotatable segment 304.

Second rotatable segment 308 is shown in detail in FIGS. 13A to 13E. Main body 350 includes a hole 352 which receives a portion of swivel segment 306. In one exemplary embodiment, third circular end 346 of swivel segment 306 is disposed in close proximity to inner wall 354. An upper slot 356 is provided, and is generally rectangular in shape. In addition, a hole 358 extends from slot wall 360 to outer wall 362. A further hole 364 is provided for use with tension clamp 314, similar to previously described hole 340 in first rotatable segment 304. Holes 358, 364 are disposed about axes 366, 368, respectively, and in one exemplary embodiment these axes are substantially parallel to each other.

A cover 370 has a serrated portion 372, an arcuate recessed portion 374, a shoulder 376, and a hole 378. Cover 370 preferably may be about the same size as upper slot 356 of second rotatable segment 308. Recessed portion 374 is configured and dimensioned to receive and retain third circular end 346 of swivel segment 306, so that end 346 may rotate therein. When cover 370 is inserted in upper slot 356, shoulder 376 preferably abuts slot wall 360. Preferably, second cylindrical portion 345 is serrated, so that serrations 372 of cover 370 engage portion 345. Moreover, an insert nut 330d with a threaded hole is provided in a seat in hole 358, and when a fastener 332 is inserted in coaxial holes 378, 358, so that the spherical lower portion of the head may be disposed in a spherical seat in hole 378, the fastener 332 threadably engages insert nut 330d. Thus, swivel segment 306 in combination with first rotatable segment 304 may freely rotate with respect to second rotatable segment 308 when fastener 332 is loose, while rotation is arrested when fastener 332 is tightened to draw serrated portion 372 of cover 370 and serrated second cylindrical portion 345 tightly together. The heads of fasteners 332 each may include a spherical lower portion to mate with a corresponding spherical recessed portion in tension clamps 312, 314 and cover 370.

While various descriptions of the present invention are described above, it should be understood that the various features can be used singly or in any combination thereof. Therefore, this invention is not to be limited to only the specifically preferred embodiments depicted herein.

Further, it should be understood that variations and modifications within the spirit and scope of the invention may occur to those skilled in the art to which the invention pertains. For example, distractor nuts, insert nuts, and lock screws may be formed integrally with the components with which they are used. The insert nuts in some cases provide threaded holes; in alternate embodiments, threading may be provided integrally with a component to obviate the need for using a threaded insert nut. Other alternate embodiments of the present invention may use different configurations of the joints disclosed herein, such as several distractor joint assemblies which may be adapted for use with components other than the distractor bar. Also, although the fixator of the present invention is described with both a distractor joint assembly and a T-clamp joint assembly, other configurations of fixators are within the scope of the present invention. One such embodiment may include one or more distractor joint assemblies, but not include a T-clamp joint assembly. Further, although a distractor clamp assembly and a T-clamp assembly are described, some fixators may have only one type of clamp assembly, or clamp assemblies other than the ones described herein. In addition, the materials described for the present invention may be modified, such as by using other radiopaque materials. Moreover, although serrations have been described for use with mutually engaging elements and/or components, other suitably textured surfaces may instead be used such as faceted surfaces. Accordingly, all modifications readily attainable by one versed in the art from the disclosure set forth herein are to be included as further embodiments of the present invention.

What is claimed is:

1. A bone fixator comprising:
   at least two clamping assemblies each for receiving at least one bone fastener;
   a main body disposed between the clamping assemblies, the main body having a joint assembly comprising:
      a male segment having first and second ends and a projection extending from the second end;
      a female segment having first and second ends, a cavity disposed proximate the first end and configured and dimensioned to receive at least a portion of the projection, and an opening connected to the cavity; and
      a cover piece configured and dimensioned to be received in the opening and capable of being positioned in the opening so that a longitudinal axis of the cover piece is coextensive with a longitudinal axis of the male segment,
      wherein when the male segment is inserted in the female segment and the cover piece is disposed in the opening, the cover piece resists removal of the projection and the male segment is releasably rotatable with respect to the female segment along a longitudinal axis of the main body and as the longitudinal axis of the male segment is coextensive with a longitudinal axis of the female segment.

2. The bone fixator of claim 1, further comprising at least one tension clamp comprising:
   a body having a borehole extending therethrough along a borehole axis and a fastener hole extending along a fastener axis transverse to the borehole axis, the body having an outer surface and an inner borehole surface;
   a slit extending along the borehole and across the fastener hole from the outer surface to the inner borehole surface, the slit defining opposed slit surfaces having a separation width; and
   a fastener configured and dimensioned to be received in the fastener hole,
   wherein the size of the borehole is adjustable by changing the separation width of the opposed slit surfaces.

3. The bone fixator of claim 1, further comprising a distractor body operatively associated with the male segment, wherein at least one of the clamping assemblies is operatively associated with the distractor body.

4. The bone fixator of claim 3, wherein at least one clamping assembly is translatable with respect to the distractor body and releasably lockable thereto.

5. The bone fixator of claim 1, wherein at least one of the clamping assemblies comprises at least one of the male or female segments.

6. A bone fixator comprising:
at least two clamping assemblies each for receiving at least one bone fastener;
a main body disposed between the clamping assemblies, the main body having a joint assembly comprising:
a male segment having first and second ends and a projection extending from the second end;
a female segment having first and second ends, a cavity disposed proximate the first end and configured and dimensioned to receive at least a portion of the projection, and an opening connected to the cavity; and
a cover piece configured and dimensioned to be received in the opening,
wherein when the male segment is inserted in the female segment and the cover piece is disposed in the opening, the cover piece resists removal of the projection and the male segment is releasable rotatable with respect to the female segment along a longitudinal axis of the main body and as a longitudinal axis of the male segment is coextensive with a longitudinal axis of the female segment, wherein the projection comprises a serrated cylindrical portion and the cover piece comprises a serrated arcuate inner surface, wherein the serrated cylindrical portion and the serrated arcuate inner surface are mutually positively lockable.

7. The bone fixator of claim 6, wherein the female segment further comprises a fastener hole and the cover piece further comprises a cover piece hole, the holes being coaxial when the cover piece is disposed in the opening.

8. The bone fixator of claim 7, further comprising a fastener, wherein when the fastener is disposed in the coaxial fastener hole and cover piece hole, the cover piece is securable to the female segment.

9. A bone fixator comprising:
at least two clamping assemblies each for receiving at least one bone fastener; and
at least one joint assembly comprising:
a first rotatable member comprising a first end, a second end and a projection having a through hole with an axis, the projection disposed at the second end;
a second rotatable member having a main body comprising a first end, a second end, a top surface, a bottom surface, a cavity disposed proximate the first end, an opening in the top surface, the opening having a bottom surface, a cover configured and dimensioned to be received in the opening, and at least one fastening means, the cover being capable of being positioned in the opening so that a longitudinal axis of the cover is coextensive with a longitudinal axis of the first rotatable member; and
a swivel member disposed between the first rotatable member and the second rotatable member, wherein the first rotatable member and the second rotatable member can rotate with respect to one another while the longitudinal axis of the first rotatable member remains coextensive with a longitudinal axis of the second rotatable member.

10. The bone fixator of claim 9, wherein the first end of the first rotatable member further comprises a through hole having an axis and wherein the axis of the through hole in the projection and the axis of the through hole in the first end are substantially perpendicular to each other.

11. The bone fixator of claim 9, wherein the swivel member comprises:
a first cylindrical end having a diameter;
a second cylindrical end having a diameter; and
a cylindrical portion disposed between the first and second cylindrical ends and having a diameter;
wherein the diameter of the second cylindrical end is greater than the diameter of the cylindrical portion, which is greater than the diameter of the first cylindrical end.

12. The bone fixator of claim 9, wherein the cavity disposed proximate the first end of the second rotatable member is in communication with the opening in the top surface of the second rotatable member.

13. The bone fixator of claim 9, wherein at least one of the clamping assemblies comprises at least one of the first or second rotatable members.

14. A bone fixator comprising:
at least two clamping assemblies each for receiving at least one bone fastener; and
at least one joint assembly comprising:
a first rotatable member comprising a first end, a second end and a projection having a through hole with an axis, the projection disposed at the second end;
a second rotatable member having a main body comprising a first end, a second end, a top surface, a bottom surface, a cavity disposed proximate the first end, an opening in the top surface, the opening having a bottom surface, a cover configured and dimensioned to be received in the opening, and at least one fastening means, the cover being capable of being positioned in the opening so that a longitudinal axis of the cover is coextensive with a longitudinal axis of the first rotatable member; and
a swivel member disposed between the first rotatable member and the second rotatable member, wherein the first rotatable member and the second rotatable member can rotate with respect to one another while a longitudinal axis of the first rotatable member remains coextensive with a longitudinal axis of the second rotatable member, wherein the swivel member comprises:
a first cylindrical end having a diameter;
a second cylindrical end having a diameter; and
a cylindrical portion disposed between the first and second cylindrical ends and having a diameter;
wherein the diameter of the second cylindrical end is greater than the diameter of the cylindrical portion, which is greater than the diameter of the first cylindrical end, wherein the projection of the first rotatable member is configured and dimensioned to receive the first cylindrical end of the swivel member and the cavity of the second rotatable member is configured and dimensioned to receive the second cylindrical end of the swivel member.

15. A bone fixator comprising:
at least two clamping assemblies each for receiving at least one bone fastener; and
at least one joint assembly comprising:
a first rotatable member comprising a first end, a second end and a projection having a through hole with an axis, the projection disposed at the second end;
a second rotatable member having a main body comprising a first end, a second end, a top surface, a bottom surface, a cavity disposed proximate the first end, an opening in the top surface, the opening having a bottom surface, a cover configured and dimensioned to be received in the opening, and at least one fastening means, the cover being capable of being positioned in the opening so that a longitudinal axis of the cover is coextensive with a longitudinal axis of the first rotatable member; and a swivel member disposed between the first rotatable member and the second rotatable member, wherein the first rotatable member and the second rotatable member can rotate with respect to one another while a longitudinal axis of the first rotatable member remains coextensive with a longitudinal axis of the second rotatable member, wherein the swivel member comprises:

a first cylindrical end having a diameter;

a second cylindrical end having a diameter; and a cylindrical portion disposed between the first and second cylindrical ends and having a diameter;

wherein the diameter of the second cylindrical end is greater than the diameter of the cylindrical portion, which is greater than the diameter of the first cylindrical end, wherein the cylindrical portion is serrated.

16. The bone fixator of claim 15, wherein the cover comprises:

a serrated portion configured and dimensioned to engage the serrations in the cylindrical portion of the swivel member;

an arcuate recessed portion configured and dimensioned to receive the second end of the swivel member;

a shoulder; and a hole;

wherein the first rotatable member in combination with the swivel member freely rotates with respect to the second rotatable member when the fastening means is loose; and wherein tightening of the fastening means draws the serrated portion of the cover and the serrations of the cylindrical portion together, thereby arresting rotation of the first rotatable member in combination with the swivel member with respect to the second rotatable member.

17. A bone fixator comprising:

at least two clamping assemblies each for receiving at least one bone fastener; and at least one joint assembly comprising:

a first rotatable member comprising a first end, a second end and a projection having a through hole with an axis, the projection disposed at the second end;

a second rotatable member having a main body comprising a first end, a second end, a top surface, a bottom surface, a cavity disposed proximate the first end, an opening in the top surface, the opening having a bottom surface, a cover configured and dimensioned to be received in the opening, and at least one fastening means; and a swivel member disposed between the first rotatable member and the second rotatable member, wherein the first rotatable member and the second rotatable member can rotate with respect to one another while a longitudinal axis of the first rotatable member remains coextensive with a longitudinal axis of the second rotatable member, the bone fixator further comprising a distractor body operatively associated with the first rotatable member, wherein at least one of the clamping assemblies is operatively associated with the distractor body.

18. The bone fixator of claim 17, wherein at least one clamping assembly is translatable with respect to the distractor body and releasably lockable thereto.

19. A bone fixator comprising:

at least two clamping assemblies each for receiving at least one bone fastener; and at least one joint assembly comprising:

a first rotatable member comprising a first end, a second end and a projection having a through hole with an axis, the projection disposed at the second end;

a second rotatable member having a main body comprising a first end, a second end, a top surface, a bottom surface, a cavity disposed proximate the first end, an opening in the top surface, the opening having a bottom surface, a cover configured and dimensioned to be received in the opening, and at least one fastening means; and a swivel member disposed between the first rotatable member and the second rotatable member, wherein the first rotatable member and the second rotatable member can rotate with respect to one another while a longitudinal axis of the first rotatable member remains coextensive with a longitudinal axis of the second rotatable member, the bone fixator further comprising at least one tension clamp comprising:

a body having a borehole extending therethrough along a borehole axis and a fastener hole extending along a fastener axis transverse to the borehole axis, the body having an outer surface and an inner borehole surface;

a slit extending along the borehole and across the fastener hole from the outer surface to the inner borehole surface, the slit defining opposed slit surfaces having a separation width; and a fastener configured and dimensioned to be received in the fastener hole, wherein the size of the borehole is adjustable by changing the separation width of the opposed slit surfaces.

20. A bone fixator comprising:

at least two clamping assemblies each for receiving at least bone fastener;

a main body disposed between the clamping assemblies, the main body having a joint assembly comprising:

a male segment having first and second ends and a projection extending from the second end;

a female segment having first and second ends, a cavity disposed proximate the first end and configured and dimensioned to receive at least a portion of the projection, and an opening connected to the cavity; and a cover piece configured and dimensioned to be received in the opening and capable of being positioned in the opening so that a longitudinal axis of the cover piece is coextensive with a longitudinal axis of the male segment, wherein when the male segment is inserted in the female segment and the cover piece is disposed in the opening, the cover piece resists removal of the projection and the male segment is releasably rotatable with respect to the female segment along a longitudinal axis of the main body and as a longitudinal axis of the male segment is coextensive with a longitudinal axis of the female segment; and at least one tension clamp comprising:

a body having a borehole extending therethrough along a borehole axis and a fastener hole extending along a fastener axis transverse to the borehole axis, the body having an outer surface and an inner borehole surface;

a slit extending along the borehole and across the fastener hole from the outer surface to the inner borehole surface, the slit defining opposed slit surfaces having a separation width; and a fastener configured and dimensioned to be received in the fastener hole;

wherein the size of the borehole is adjustable by changing the separation width of the opposed slit surfaces.

* * * * *